(12) United States Patent
Baldasarre et al.

(10) Patent No.: US 12,197,681 B2
(45) Date of Patent: Jan. 14, 2025

(54) ANCHOR CONFIGURATIONS FOR AN ARRAY OF ULTRASONIC TRANSDUCERS

(71) Applicant: TDK CORPORATION, Tokyo (JP)

(72) Inventors: Leonardo Baldasarre, Varese (IT); Alessandro Colombo, Milan (IT); Federica Confalonieri, Carimate (IT); Marco Travagliati, Pavia (IT)

(73) Assignee: TDK CORPORATION, Tokyo (JP)

( * ) Notice: Subject to any disclaimer, the term of this patent is extended or adjusted under 35 U.S.C. 154(b) by 119 days.

(21) Appl. No.: 17/822,127

(22) Filed: Aug. 24, 2022

(65) Prior Publication Data

US 2023/0067383 A1   Mar. 2, 2023

Related U.S. Application Data

(60) Provisional application No. 63/260,571, filed on Aug. 25, 2021.

(51) Int. Cl.
*G06F 3/043* (2006.01)
*A61B 8/00* (2006.01)
(Continued)

(52) U.S. Cl.
CPC .......... *G06F 3/0436* (2013.01); *A61B 8/4483* (2013.01); *B06B 1/0207* (2013.01);
(Continued)

(58) Field of Classification Search
CPC ..... G06F 3/0346; G06V 40/1306; A61B 8/00; A61B 8/4483; B06B 1/0207
See application file for complete search history.

(56) References Cited

U.S. PATENT DOCUMENTS

| 4,880,012 A | 11/1989 | Sato |
|---|---|---|
| 5,575,286 A | 11/1996 | Weng et al. |

(Continued)

FOREIGN PATENT DOCUMENTS

| CN | 1826631 A | 8/2006 |
|---|---|---|
| CN | 101192644 A | 6/2008 |

(Continued)

OTHER PUBLICATIONS

Tang, et al., "Pulse-Echo Ultrasonic Fingerprint Sensor on a Chip", IEEE Transducers, Anchorage, Alaska, USA, Jun. 21-25, 2015, pp. 674-677.

(Continued)

*Primary Examiner* — Chao Sheng

(57) ABSTRACT

An ultrasonic transducer array including a substrate, a membrane overlying the substrate, the membrane configured to allow movement at ultrasonic frequencies, and a plurality of anchors connected to the substrate and connected to the membrane. The membrane includes a piezoelectric layer, a plurality of first electrodes, and a plurality of second electrodes, wherein each ultrasonic transducer of a plurality of ultrasonic transducers includes at least a first electrode and at least a second electrode. The plurality of anchors includes a first anchor including a first electrical connection for electrically coupling at least one first electrode to control circuitry and a second anchor including a second electrical connection for electrically coupling at least one second electrode. The ultrasonic transducer array could be either a two-dimensional array or a one-dimensional array of ultrasonic transducers.

22 Claims, 11 Drawing Sheets

(51) Int. Cl.
  *B06B 1/02* (2006.01)
  *G06V 40/13* (2022.01)
  *B06B 1/06* (2006.01)

(52) U.S. Cl.
  CPC ............ *G06V 40/1306* (2022.01); *A61B 8/00* (2013.01); *B06B 1/064* (2013.01)

(56) References Cited

U.S. PATENT DOCUMENTS

| | | |
|---|---|---|
| 5,680,863 A | 10/1997 | Hossack et al. |
| 5,684,243 A | 11/1997 | Gururaja et al. |
| 5,808,967 A | 9/1998 | Yu et al. |
| 5,867,302 A | 2/1999 | Fleming |
| 5,911,692 A | 6/1999 | Hussain et al. |
| 6,071,239 A | 6/2000 | Cribbs et al. |
| 6,104,673 A | 8/2000 | Cole et al. |
| 6,289,112 B1 | 9/2001 | Jain et al. |
| 6,292,576 B1 | 9/2001 | Brownlee |
| 6,296,610 B1 | 10/2001 | Schneider et al. |
| 6,350,652 B1 | 2/2002 | Libera et al. |
| 6,428,477 B1 | 8/2002 | Mason |
| 6,483,932 B1 | 11/2002 | Martinez et al. |
| 6,500,120 B1 | 12/2002 | Anthony |
| 6,676,602 B1 | 1/2004 | Barnes et al. |
| 6,679,844 B2 | 1/2004 | Loftman et al. |
| 6,736,779 B1 | 5/2004 | Sano et al. |
| 7,067,962 B2 | 6/2006 | Scott |
| 7,109,642 B2 | 9/2006 | Scott |
| 7,243,547 B2 | 7/2007 | Cobianu et al. |
| 7,257,241 B2 | 8/2007 | Lo |
| 7,400,750 B2 | 7/2008 | Nam |
| 7,433,034 B1 | 10/2008 | Huang |
| 7,459,836 B2 | 12/2008 | Scott |
| 7,471,034 B2 | 12/2008 | Schlote-Holubek et al. |
| 7,489,066 B2 | 2/2009 | Scott et al. |
| 7,634,117 B2 | 12/2009 | Cho |
| 7,665,763 B2 | 2/2010 | Bjoerklund et al. |
| 7,739,912 B2 | 6/2010 | Schneider et al. |
| 7,914,454 B2 | 3/2011 | Weber et al. |
| 8,018,010 B2 | 9/2011 | Tigli et al. |
| 8,139,827 B2 | 3/2012 | Schneider et al. |
| 8,255,698 B2 | 8/2012 | Li et al. |
| 8,311,514 B2 | 11/2012 | Bandyopadhyay et al. |
| 8,335,356 B2 | 12/2012 | Schmitt |
| 8,433,110 B2 | 4/2013 | Kropp et al. |
| 8,508,103 B2 | 8/2013 | Schmitt et al. |
| 8,515,135 B2 | 8/2013 | Clarke et al. |
| 8,666,126 B2 | 3/2014 | Lee et al. |
| 8,703,040 B2 | 4/2014 | Liufu et al. |
| 8,723,399 B2 | 5/2014 | Sammoura et al. |
| 8,805,031 B2 | 8/2014 | Schmitt |
| 9,056,082 B2 | 6/2015 | Liautaud et al. |
| 9,070,861 B2 | 6/2015 | Bibl et al. |
| 9,224,030 B2 | 12/2015 | Du et al. |
| 9,245,165 B2 | 1/2016 | Slaby et al. |
| 9,424,456 B1 | 8/2016 | Kamath Koteshwara et al. |
| 9,572,549 B2 | 2/2017 | Belevich et al. |
| 9,582,102 B2 | 2/2017 | Setlak |
| 9,582,705 B2 | 2/2017 | Du et al. |
| 9,607,203 B1 | 3/2017 | Yazdandoost et al. |
| 9,607,206 B2 | 3/2017 | Schmitt et al. |
| 9,613,246 B1 | 4/2017 | Gozzini et al. |
| 9,618,405 B2 | 4/2017 | Liu et al. |
| 9,665,763 B2 | 5/2017 | Du et al. |
| 9,747,488 B2 | 8/2017 | Yazdandoost et al. |
| 9,785,819 B1 | 10/2017 | Oreifej |
| 9,815,087 B2 | 11/2017 | Ganti et al. |
| 9,817,108 B2 | 11/2017 | Kuo et al. |
| 9,818,020 B2 | 11/2017 | Schuckers et al. |
| 9,881,195 B2 | 1/2018 | Lee et al. |
| 9,881,198 B2 | 1/2018 | Lee et al. |
| 9,898,640 B2 | 2/2018 | Ghavanini |
| 9,904,836 B2 | 2/2018 | Yeke Yazdandoost et al. |
| 9,909,225 B2 | 3/2018 | Lee et al. |
| 9,922,235 B2 | 3/2018 | Cho et al. |
| 9,933,319 B2 | 4/2018 | Li et al. |
| 9,934,371 B2 | 4/2018 | Hong et al. |
| 9,939,972 B2 | 4/2018 | Shepelev et al. |
| 9,953,205 B1 | 4/2018 | Rasmussen et al. |
| 9,959,444 B2 | 5/2018 | Young et al. |
| 9,967,100 B2 | 5/2018 | Hong et al. |
| 9,983,656 B2 | 5/2018 | Merrell et al. |
| 9,984,271 B1 | 5/2018 | King et al. |
| 10,006,824 B2 | 6/2018 | Tsai et al. |
| 10,080,544 B2 | 9/2018 | Chiang et al. |
| 10,275,638 B1 | 4/2019 | Yousefpor et al. |
| 10,315,222 B2 | 6/2019 | Salvia et al. |
| 10,322,929 B2 | 6/2019 | Soundara Pandian et al. |
| 10,325,915 B2 | 6/2019 | Salvia et al. |
| 10,387,704 B2 | 8/2019 | Dagan et al. |
| 10,445,547 B2 | 10/2019 | Tsai |
| 10,461,124 B2 | 10/2019 | Berger et al. |
| 10,478,858 B2 | 11/2019 | Lasiter et al. |
| 10,488,274 B2 | 11/2019 | Li et al. |
| 10,497,747 B2 | 12/2019 | Tsai et al. |
| 10,515,255 B2 | 12/2019 | Strohmann et al. |
| 10,539,539 B2 | 1/2020 | Garlepp et al. |
| 10,562,070 B2 | 2/2020 | Garlepp et al. |
| 10,600,403 B2 | 3/2020 | Garlepp et al. |
| 10,643,052 B2 | 5/2020 | Garlepp et al. |
| 10,656,255 B2 | 5/2020 | Ng et al. |
| 10,670,716 B2 | 6/2020 | Apte et al. |
| 10,706,835 B2 | 7/2020 | Garlepp et al. |
| 10,726,231 B2 | 7/2020 | Tsai et al. |
| 10,755,067 B2 | 8/2020 | De Foras et al. |
| 11,107,858 B2 | 8/2021 | Berger et al. |
| 11,112,388 B2 | 9/2021 | Garlepp et al. |
| 11,301,552 B2 | 4/2022 | Gurin et al. |
| 2001/0016686 A1 | 8/2001 | Okada et al. |
| 2001/0051772 A1 | 12/2001 | Bae |
| 2002/0062086 A1 | 5/2002 | Miele et al. |
| 2002/0135273 A1 | 9/2002 | Mauchamp et al. |
| 2003/0013955 A1 | 1/2003 | Poland |
| 2004/0059220 A1 | 3/2004 | Mourad et al. |
| 2004/0085858 A1 | 5/2004 | Khuri-Yakub et al. |
| 2004/0122316 A1 | 6/2004 | Satoh et al. |
| 2004/0174773 A1 | 9/2004 | Thomenius et al. |
| 2005/0023937 A1 | 2/2005 | Sashida et al. |
| 2005/0057284 A1 | 3/2005 | Wodnicki |
| 2005/0094490 A1 | 5/2005 | Thomenius et al. |
| 2005/0100200 A1 | 5/2005 | Abiko et al. |
| 2005/0110071 A1 | 5/2005 | Ema et al. |
| 2005/0146240 A1 | 7/2005 | Smith et al. |
| 2005/0148132 A1 | 7/2005 | Wodnicki et al. |
| 2005/0162040 A1 | 7/2005 | Robert |
| 2005/0228277 A1 | 10/2005 | Barnes et al. |
| 2006/0052697 A1 | 3/2006 | Hossack et al. |
| 2006/0079773 A1 | 4/2006 | Mourad et al. |
| 2006/0079777 A1 | 4/2006 | Karasawa |
| 2006/0210130 A1 | 9/2006 | Germond-Rouet et al. |
| 2006/0230605 A1 | 10/2006 | Schlote-Holubek et al. |
| 2006/0280346 A1 | 12/2006 | Machida |
| 2007/0016026 A1 | 1/2007 | Thomenius et al. |
| 2007/0046396 A1 | 3/2007 | Huang |
| 2007/0047785 A1 | 3/2007 | Jang et al. |
| 2007/0073135 A1 | 3/2007 | Lee et al. |
| 2007/0164632 A1 | 7/2007 | Adachi et al. |
| 2007/0202252 A1 | 8/2007 | Sasaki |
| 2007/0215964 A1 | 9/2007 | Khuri-Yakub et al. |
| 2007/0223791 A1 | 9/2007 | Shinzaki |
| 2007/0230754 A1 | 10/2007 | Jain et al. |
| 2008/0125660 A1 | 5/2008 | Yao et al. |
| 2008/0146938 A1 | 6/2008 | Hazard et al. |
| 2008/0150032 A1 | 6/2008 | Tanaka |
| 2008/0194053 A1 | 8/2008 | Huang |
| 2008/0240523 A1 | 10/2008 | Benkley et al. |
| 2009/0005684 A1 | 1/2009 | Kristoffersen et al. |
| 2009/0163805 A1 | 6/2009 | Sunagawa et al. |
| 2009/0171213 A1 | 7/2009 | Savord |
| 2009/0182237 A1 | 7/2009 | Angelsen et al. |
| 2009/0232367 A1 | 9/2009 | Shinzaki |
| 2009/0274343 A1 | 11/2009 | Clarke |
| 2009/0303838 A1 | 12/2009 | Svet |
| 2010/0030076 A1 | 2/2010 | Vortman et al. |

(56) References Cited

U.S. PATENT DOCUMENTS

| | | |
|---|---|---|
| 2010/0046810 A1 | 2/2010 | Yamada |
| 2010/0063391 A1 | 3/2010 | Kanai et al. |
| 2010/0113952 A1 | 5/2010 | Raguin et al. |
| 2010/0168583 A1 | 7/2010 | Dausch et al. |
| 2010/0195851 A1 | 8/2010 | Buccafusca |
| 2010/0201222 A1 | 8/2010 | Adachi et al. |
| 2010/0202254 A1 | 8/2010 | Roest et al. |
| 2010/0208004 A1 | 8/2010 | Ottosson et al. |
| 2010/0239751 A1 | 9/2010 | Regniere |
| 2010/0251824 A1 | 10/2010 | Schneider et al. |
| 2010/0256498 A1 | 10/2010 | Tanaka |
| 2010/0278008 A1 | 11/2010 | Ammar |
| 2011/0285244 A1 | 11/2011 | Lewis et al. |
| 2011/0291207 A1 | 12/2011 | Martin et al. |
| 2011/0319767 A1 | 12/2011 | Tsuruno |
| 2012/0016604 A1 | 1/2012 | Irving et al. |
| 2012/0092026 A1 | 4/2012 | Liautaud et al. |
| 2012/0095335 A1 | 4/2012 | Sverdlik et al. |
| 2012/0095344 A1 | 4/2012 | Kristoffersen et al. |
| 2012/0095347 A1 | 4/2012 | Adam et al. |
| 2012/0147698 A1 | 6/2012 | Wong et al. |
| 2012/0179044 A1 | 7/2012 | Chiang et al. |
| 2012/0224041 A1 | 9/2012 | Monden |
| 2012/0232396 A1 | 9/2012 | Tanabe |
| 2012/0238876 A1 | 9/2012 | Tanabe et al. |
| 2012/0263355 A1 | 10/2012 | Monden |
| 2012/0279865 A1 | 11/2012 | Regniere et al. |
| 2012/0288641 A1 | 11/2012 | Diatezua et al. |
| 2012/0300988 A1 | 11/2012 | Ivanov et al. |
| 2013/0051179 A1 | 2/2013 | Hong |
| 2013/0064043 A1 | 3/2013 | Degertekin et al. |
| 2013/0127297 A1 | 5/2013 | Bautista et al. |
| 2013/0127592 A1 | 5/2013 | Fyke et al. |
| 2013/0133428 A1 | 5/2013 | Lee et al. |
| 2013/0201134 A1 | 8/2013 | Schneider et al. |
| 2013/0271628 A1 | 10/2013 | Ku et al. |
| 2013/0294201 A1 | 11/2013 | Hajati |
| 2013/0294202 A1 | 11/2013 | Hajati |
| 2014/0003679 A1 | 1/2014 | Han et al. |
| 2014/0060196 A1 | 3/2014 | Falter et al. |
| 2014/0117812 A1 | 5/2014 | Hajati |
| 2014/0176332 A1 | 6/2014 | Alameh et al. |
| 2014/0208853 A1 | 7/2014 | Onishi et al. |
| 2014/0219521 A1 | 8/2014 | Schmitt et al. |
| 2014/0232241 A1 | 8/2014 | Hajati |
| 2014/0265721 A1 | 9/2014 | Robinson et al. |
| 2014/0294262 A1 | 10/2014 | Schuckers et al. |
| 2014/0313007 A1 | 10/2014 | Harding |
| 2014/0355387 A1 | 12/2014 | Kitchens et al. |
| 2015/0036065 A1 | 2/2015 | Yousefpor et al. |
| 2015/0049590 A1 | 2/2015 | Rowe et al. |
| 2015/0087991 A1 | 3/2015 | Chen et al. |
| 2015/0097468 A1 | 4/2015 | Hajati et al. |
| 2015/0105663 A1 | 4/2015 | Kiyose et al. |
| 2015/0127965 A1 | 5/2015 | Hong et al. |
| 2015/0145374 A1 | 5/2015 | Xu et al. |
| 2015/0164473 A1 | 6/2015 | Kim et al. |
| 2015/0165479 A1 | 6/2015 | Lasiter et al. |
| 2015/0169136 A1 | 6/2015 | Ganti et al. |
| 2015/0189136 A1 | 7/2015 | Chung et al. |
| 2015/0198699 A1 | 7/2015 | Kuo et al. |
| 2015/0206738 A1 | 7/2015 | Rastegar |
| 2015/0213180 A1 | 7/2015 | Herberholz |
| 2015/0220767 A1 | 8/2015 | Yoon et al. |
| 2015/0241393 A1 | 8/2015 | Ganti et al. |
| 2015/0261261 A1 | 9/2015 | Bhagavatula et al. |
| 2015/0286312 A1 | 10/2015 | Kang et al. |
| 2015/0301653 A1 | 10/2015 | Urushi |
| 2015/0324569 A1 | 11/2015 | Hong et al. |
| 2015/0345987 A1 | 12/2015 | Hajati |
| 2015/0357375 A1 | 12/2015 | Tsai et al. |
| 2015/0358740 A1 | 12/2015 | Tsai et al. |
| 2015/0362589 A1 | 12/2015 | Tsai |
| 2015/0371398 A1 | 12/2015 | Qiao et al. |
| 2016/0026840 A1 | 1/2016 | Li et al. |
| 2016/0041047 A1 | 2/2016 | Liu et al. |
| 2016/0051225 A1 | 2/2016 | Kim et al. |
| 2016/0063294 A1 | 3/2016 | Du et al. |
| 2016/0063300 A1 | 3/2016 | Du et al. |
| 2016/0070967 A1 | 3/2016 | Du et al. |
| 2016/0070968 A1 | 3/2016 | Gu et al. |
| 2016/0086010 A1 | 3/2016 | Merrell et al. |
| 2016/0091378 A1 | 3/2016 | Tsai et al. |
| 2016/0092715 A1 | 3/2016 | Yazdandoost et al. |
| 2016/0092716 A1 | 3/2016 | Yazdandoost et al. |
| 2016/0100822 A1 | 4/2016 | Kim et al. |
| 2016/0107194 A1* | 4/2016 | Panchawagh ......... B06B 1/0666 310/317 |
| 2016/0117541 A1 | 4/2016 | Lu et al. |
| 2016/0180142 A1 | 6/2016 | Riddle et al. |
| 2016/0240768 A1 | 8/2016 | Fujii et al. |
| 2016/0296975 A1 | 10/2016 | Lukacs et al. |
| 2016/0299014 A1 | 10/2016 | Li et al. |
| 2016/0326477 A1 | 11/2016 | Fernandez-Alcon et al. |
| 2016/0345930 A1 | 12/2016 | Mizukami et al. |
| 2016/0350573 A1 | 12/2016 | Kitchens et al. |
| 2016/0358003 A1 | 12/2016 | Shen et al. |
| 2017/0004346 A1 | 1/2017 | Kim et al. |
| 2017/0004352 A1 | 1/2017 | Jonsson et al. |
| 2017/0330552 A1 | 1/2017 | Garlepp et al. |
| 2017/0032485 A1 | 2/2017 | Vemury |
| 2017/0059380 A1 | 3/2017 | Li et al. |
| 2017/0075700 A1 | 3/2017 | Abudi et al. |
| 2017/0076132 A1 | 3/2017 | Sezan et al. |
| 2017/0090024 A1 | 3/2017 | Kitchens et al. |
| 2017/0100091 A1 | 4/2017 | Eigil et al. |
| 2017/0110504 A1 | 4/2017 | Panchawagh et al. |
| 2017/0119343 A1 | 5/2017 | Pintoffl |
| 2017/0124374 A1 | 5/2017 | Rowe et al. |
| 2017/0168543 A1 | 6/2017 | Dai et al. |
| 2017/0185821 A1 | 6/2017 | Chen et al. |
| 2017/0194934 A1 | 7/2017 | Shelton et al. |
| 2017/0200054 A1 | 7/2017 | Du et al. |
| 2017/0219536 A1 | 8/2017 | Koch et al. |
| 2017/0231534 A1 | 8/2017 | Agassy et al. |
| 2017/0243049 A1 | 8/2017 | Dong |
| 2017/0255338 A1 | 9/2017 | Medina et al. |
| 2017/0293791 A1 | 10/2017 | Mainguet et al. |
| 2017/0316243 A1 | 11/2017 | Ghavanini |
| 2017/0316248 A1 | 11/2017 | He et al. |
| 2017/0322290 A1 | 11/2017 | Ng |
| 2017/0322291 A1* | 11/2017 | Salvia ................ G06V 40/1306 |
| 2017/0322292 A1 | 11/2017 | Salvia et al. |
| 2017/0322305 A1 | 11/2017 | Apte et al. |
| 2017/0323133 A1 | 11/2017 | Tsai |
| 2017/0325081 A1 | 11/2017 | Chrisikos et al. |
| 2017/0326590 A1 | 11/2017 | Daneman |
| 2017/0326591 A1 | 11/2017 | Apte et al. |
| 2017/0326593 A1 | 11/2017 | Garlepp et al. |
| 2017/0326594 A1 | 11/2017 | Berger et al. |
| 2017/0328866 A1 | 11/2017 | Apte et al. |
| 2017/0328870 A1 | 11/2017 | Garlepp et al. |
| 2017/0330012 A1 | 11/2017 | Salvia et al. |
| 2017/0330553 A1 | 11/2017 | Garlepp et al. |
| 2017/0344782 A1 | 11/2017 | Andersson |
| 2017/0357839 A1 | 12/2017 | Yazdandoost et al. |
| 2017/0368574 A1 | 12/2017 | Sammoura et al. |
| 2018/0025202 A1 | 1/2018 | Ryshtun et al. |
| 2018/0032788 A1 | 2/2018 | Krenzer et al. |
| 2018/0069168 A1 | 3/2018 | Ikeuchi et al. |
| 2018/0101711 A1 | 4/2018 | D'Souza et al. |
| 2018/0107852 A1 | 4/2018 | Fenrich et al. |
| 2018/0107854 A1 | 4/2018 | Tsai et al. |
| 2018/0129849 A1 | 5/2018 | Strohmann et al. |
| 2018/0129857 A1 | 5/2018 | Bonev |
| 2018/0150679 A1 | 5/2018 | Kim et al. |
| 2018/0178251 A1 | 6/2018 | Foncellino et al. |
| 2018/0206820 A1 | 7/2018 | Anand et al. |
| 2018/0217008 A1 | 8/2018 | Li et al. |
| 2018/0225495 A1 | 8/2018 | Jonsson et al. |
| 2018/0229267 A1 | 8/2018 | Ono et al. |
| 2018/0268232 A1 | 9/2018 | Kim et al. |
| 2018/0276443 A1 | 9/2018 | Strohmann et al. |
| 2018/0276672 A1 | 9/2018 | Breed et al. |

(56) References Cited

U.S. PATENT DOCUMENTS

| | | |
|---|---|---|
| 2018/0329560 A1 | 11/2018 | Kim et al. |
| 2018/0341799 A1 | 11/2018 | Schwartz et al. |
| 2018/0349663 A1 | 12/2018 | Garlepp et al. |
| 2018/0357457 A1 | 12/2018 | Rasmussen et al. |
| 2018/0369866 A1 | 12/2018 | Sammoura et al. |
| 2018/0373913 A1 | 12/2018 | Panchawagh et al. |
| 2018/0376253 A1 | 12/2018 | Lutsky et al. |
| 2019/0005300 A1 | 1/2019 | Garlepp et al. |
| 2019/0012673 A1 | 1/2019 | Chakraborty et al. |
| 2019/0018123 A1 | 1/2019 | Narasimha-Iyer et al. |
| 2019/0043920 A1 | 2/2019 | Berger et al. |
| 2019/0046263 A1 | 2/2019 | Hayashida et al. |
| 2019/0057267 A1 | 2/2019 | Kitchens et al. |
| 2019/0073507 A1 | 3/2019 | D'Souza et al. |
| 2019/0087632 A1 | 3/2019 | Raguin et al. |
| 2019/0095015 A1 | 3/2019 | Han et al. |
| 2019/0102046 A1 | 4/2019 | Miranto et al. |
| 2019/0130083 A1 | 5/2019 | Agassy et al. |
| 2019/0148619 A1 | 5/2019 | Ikeuchi et al. |
| 2019/0171858 A1 | 6/2019 | Ataya et al. |
| 2019/0175035 A1 | 6/2019 | Van Der Horst et al. |
| 2019/0180069 A1 | 6/2019 | Akhbari et al. |
| 2019/0188441 A1 | 6/2019 | Hall et al. |
| 2019/0188442 A1 | 6/2019 | Flament et al. |
| 2019/0247887 A1 | 8/2019 | Salvia et al. |
| 2019/0262865 A1 | 8/2019 | Mehdizadeh et al. |
| 2019/0311177 A1 | 10/2019 | Joo et al. |
| 2019/0325185 A1 | 10/2019 | Tang |
| 2019/0340455 A1 | 11/2019 | Jung et al. |
| 2019/0354238 A1 | 11/2019 | Akhbari et al. |
| 2019/0370518 A1 | 12/2019 | Maor et al. |
| 2020/0030850 A1 | 1/2020 | Apte et al. |
| 2020/0050816 A1 | 2/2020 | Tsai |
| 2020/0050817 A1 | 2/2020 | Salvia et al. |
| 2020/0050820 A1 | 2/2020 | Iatsun et al. |
| 2020/0050828 A1 | 2/2020 | Li et al. |
| 2020/0074135 A1 | 3/2020 | Garlepp et al. |
| 2020/0111834 A1 | 4/2020 | Tsai et al. |
| 2020/0125710 A1 | 4/2020 | Andersson et al. |
| 2020/0147644 A1* | 5/2020 | Chang ............... B06B 1/0666 |
| 2020/0158694 A1 | 5/2020 | Garlepp et al. |
| 2020/0175143 A1 | 6/2020 | Lee et al. |
| 2020/0194495 A1 | 6/2020 | Berger et al. |
| 2020/0210666 A1 | 7/2020 | Flament |
| 2020/0250393 A1 | 8/2020 | Tsai et al. |
| 2020/0257875 A1 | 8/2020 | Hall et al. |
| 2020/0285882 A1 | 9/2020 | Skovgaard Christensen et al. |
| 2020/0302140 A1 | 9/2020 | Lu et al. |
| 2020/0342203 A1 | 10/2020 | Lin et al. |
| 2020/0355824 A1 | 11/2020 | Apte et al. |
| 2020/0400800 A1 | 12/2020 | Ng et al. |
| 2020/0410070 A1 | 12/2020 | Strohmann |
| 2020/0410193 A1 | 12/2020 | Wu |
| 2021/0015456 A1 | 1/2021 | Chiang et al. |
| 2021/0069748 A1 | 3/2021 | Bircumshaw et al. |
| 2021/0161503 A1 | 6/2021 | Mashood et al. |
| 2021/0177378 A1 | 6/2021 | Goericke et al. |
| 2022/0043144 A1 | 2/2022 | Yanni et al. |
| 2022/0262161 A1 | 8/2022 | Zhao et al. |

FOREIGN PATENT DOCUMENTS

| | | |
|---|---|---|
| CN | 102159334 A | 8/2011 |
| CN | 104415902 A | 3/2015 |
| CN | 105264542 A | 1/2016 |
| CN | 105378756 A | 3/2016 |
| CN | 106458575 B | 7/2018 |
| CN | 109196671 A | 1/2019 |
| CN | 109255323 A | 1/2019 |
| CN | 112241657 A | 1/2021 |
| EP | 1214909 A1 | 6/2002 |
| EP | 1768101 A1 | 3/2007 |
| EP | 2884301 A1 | 6/2015 |
| EP | 3086261 A2 | 10/2016 |
| EP | 1534140 B1 | 1/2019 |
| EP | 3292508 B1 | 12/2020 |
| EP | 3757884 A1 | 12/2020 |
| JP | 2011040467 A | 2/2011 |
| JP | 2014183229 A | 9/2014 |
| KR | 20200090355 A | 7/2020 |
| NO | 2017053877 A2 | 3/2017 |
| TW | 201531701 A | 8/2015 |
| WO | 2007018635 A1 | 2/2007 |
| WO | 2009096576 A2 | 8/2009 |
| WO | 2009137106 A2 | 11/2009 |
| WO | 2014035564 A1 | 3/2014 |
| WO | 2015009635 A1 | 1/2015 |
| WO | 2015112453 A1 | 7/2015 |
| WO | 2015120132 A1 | 8/2015 |
| WO | 2015131083 A1 | 9/2015 |
| WO | 2015134816 A1 | 9/2015 |
| WO | 2015183945 A1 | 12/2015 |
| WO | 2015193917 A2 | 12/2015 |
| WO | 2016007250 A1 | 1/2016 |
| WO | 2016011172 A1 | 1/2016 |
| WO | 2016022439 A1 | 2/2016 |
| WO | 2016040333 A2 | 3/2016 |
| WO | 2016053587 A1 | 4/2016 |
| WO | 2016061406 A1 | 4/2016 |
| WO | 2016061410 A1 | 4/2016 |
| WO | 2017003848 A1 | 1/2017 |
| WO | 2017192890 A1 | 11/2017 |
| WO | 2017192895 A1 | 11/2017 |
| WO | 2017192899 A1 | 11/2017 |
| WO | 2017196678 A1 | 11/2017 |
| WO | 2017196681 A1 | 11/2017 |
| WO | 2017196682 A1 | 11/2017 |
| WO | 2017192903 A3 | 12/2017 |
| WO | 2018148332 A1 | 8/2018 |
| WO | 2019005487 A1 | 1/2019 |
| WO | 2019164721 A1 | 8/2019 |
| WO | 2020081182 A1 | 4/2020 |

OTHER PUBLICATIONS

ISA/EP, International Search Report and Written Opinion for International Application # PCT/US2018/063431, pp. 1-15, mailed Feb. 5, 2019.

ISA/EP, International Search Report and Written Opinion for International Application No. PCT/US2017/031120, 12 pages, Aug. 29, 2017.

ISA/EP, International Search Report and Written Opinion for International Application No. PCT/US2017/031127, 13 pages, Sep. 1, 2017.

ISA/EP, International Search Report and Written Opinion for International Application No. PCT/US2017/031134, 12 pages, Aug. 30, 2017.

ISA/EP, International Search Report and Written Opinion for International Application No. PCT/US2017/031140, 18 pages, Nov. 2, 2017.

ISA/EP, International Search Report and Written Opinion for International Application No. PCT/US2017/031421 13 pages, Jun. 21, 2017.

ISA/EP, International Search Report and Written Opinion for International Application No. PCT/US2017/031426 13 pages, Jun. 22, 2017.

ISA/EP, International Search Report and Written Opinion for International Application No. PCT/US2017/031431, 14 pages, Aug. 1, 2017.

ISA/EP, International Search Report and Written Opinion for International Application No. PCT/US2017/031434, 13 pages, Jun. 26, 2017.

ISA/EP, International Search Report and Written Opinion for International Application No. PCT/US2017/031439, 10 pages Jun. 20, 2017.

ISA/EP, International Search Report and Written Opinion for International Application No. PCT/US2017/031824, 18 pages, Sep. 22, 2017.

ISA/EP, International Search Report and Written Opinion for International Application No. PCT/US2017/031827, 16 pages, Aug. 1, 2017.

(56) References Cited

OTHER PUBLICATIONS

ISA/EP, International Search Report and Written Opinion for International Application No. PCT/US2017/031831, 12 pages, Jul. 21, 2017.

ISA/EP, International Search Report for International Application No. PCT/US2017/031826, 16 pages, Feb. 27, 2018.

ISA/EP, Partial International Search Report for International Application No. PCT/US2017/031140, 13 pages, Aug. 29, 2017.

ISA/EP, Partial International Search Report for International Application No. PCT/US2017/031823, 12 pages, Nov. 30, 2017.

"Receiver Thermal Noise Threshold", Fisher Telecommunication Services, Satellite Communications. Retrieved from the Internet: URL:https://web.archive.org/web/20171027075705/http//www.fishercom.xyz:80/satellite-communications/receiver-thermal-noise-threshold.html, Oct. 27, 2017, 3.

"ZTE V7 Max. 5,5" smartphone on MediaTeck Helio P10 cpu; Published on Apr. 20, 2016; https://www.youtube.com/watch?v=ncNCbpkGQZU (Year: 2016).

Dausch, et al., "Theory and Operation of 2-D Array Piezoelectric Micromachined Ultrasound Transducers", IEEE Transactions on Ultrasonics, and Frequency Control, vol. 55, No. 11;, Nov. 2008, 2484-2492.

Hopcroft, et al., "Temperature Compensation of a MEMS Resonator Using Quality Factor as a Thermometer", Retrieved from Internet: http://micromachine.stanford.edu/~amanu/linked/MAH_MEMS2006.pdf, 2006, 222-225.

Hopcroft, et al., "Using the temperature dependence of resonator quality factor as a thermometer", Applied Physics Letters 91. Retrieved from Internet: http://micromachine.stanford.edu/~hopcroft/Publications/Hopcroft_QT_ApplPhysLett_91_013505.pdf, 2007, 013505-1-031505-3.

Lee, et al., "Low jitter and temperature stable MEMS oscillators", Frequency Control Symposium (FCS), 2012 IEEE International, May 2012, 1-5.

Li, et al., "Capacitive micromachined ultrasonic transducer for ultra-low pressure measurement: Theoretical study", AIP Advances 5.12. Retrieved from Internet: http://scitation.aip.org/content/aip/journal/adva/5/12/10.1063/1.4939217, 2015, 127231.

Qiu, et al., "Piezoelectric Micromachined Ultrasound Transducer (PMUT) Arrays for Integrated Sensing, Actuation and Imaging", Sensors 15, doi: 10.3390/s150408020, Apr. 3, 2015, 8020-8041.

Rozen, et al., "Air-Coupled Aluminum Nitride Piezoelectric Micromachined Ultrasonic Transducers at 0.3 Mhz to 0.9 MHZ", 2015 28th IEEE International Conference on Micro Electro Mechanical Systems (MEMS), IEEE, Jan. 18, 2015, 921-924.

Savoia, et al., "Design and Fabrication of a cMUT Probe for Ultrasound Imaging of Fingerprints", 2010 IEEE International Ultrasonics Symposium Proceedings, Oct. 2010, 1877-1880.

Shen, et al., "Anisotropic Complementary Acoustic Metamaterial for Canceling out Aberrating Layers", American Physical Society, Physical Review X 4.4: 041033., Nov. 19, 2014, 041033-1-041033-7.

Tang, et al., "11.2 3D Ultrasonic Fingerprint Sensor-on-a-Chip", 2016 IEEE International Solid-State Circuits Conference, IEEE, Jan. 31, 2016, 202-203.

Thakar, et al., "Multi-resonator approach to eliminating the temperature dependence of silicon-based timing references", Hilton Head'14. Retrieved from the Internet: http://blog.narotama.ac.id/wp-content/uploads/2014/12/Multi-resonator-approach-to-eliminating-the-temperature-dependance-of-silicon-based-timing-references.pdf, 2014, 415-418.

ISA/EP, Partial International Search Report for International Application No. PCT/US2019/034032, 8 pages, Sep. 12, 2019, 8.

EP Office Action, for Application 17724184.1, mailed Oct. 12, 2021, 6 pages.

EP Office Action, for Application 17725017.2 mailed Feb. 25, 2022, 7 pages.

EP Office Action, mailed Oct. 9, 2021, 6 pages.

European Patent Office, Office Action, U.S. Appl. No. 17/725,018, pp. 5, Oct. 25, 2021.

European Patent Office, Office Action, App 17725020.6, pp. 4, Oct. 25, 2021.

ISA/EP, International Search Report and Written Opinion for International Application # PCT/US2019/015020, pp. 1-23, mailed Jul. 1, 2019.

ISA/EP, International Search Report and Written Opinion for International Application # PCT/US2019/023440, pp. 1-10, mailed Jun. 4, 2019.

ISA/EP, International Search Report and Written Opinion for International Application No. PCT/US2018/037364, 10 pages, Sep. 3, 2018.

ISA/EP, International Search Report and Written Opinion for International Application No. PCT/US2019061516, 14 pages, Mar. 12, 2020.

ISA/EP, International Search Report and Written Opinion for International Application No. PCT/US2020/033854, 16 pages, Nov. 3, 2020.

ISA/EP, International Search Report and Written Opinion for International Application No. PCT/US2020/039208, 10 pages, Oct. 9, 2020.

ISA/EP, International Search Report and Written Opinion for International Application No. PCT/US2020/039452, 11 pages, Sep. 9, 2020.

ISA/EP, International Search Report and Written Opinion for International Application No. PCT/US2020/042427, 18 pages, Dec. 14, 2020.

ISA/EP, International Search Report and Written Opinion for International Application No. PCT/US2020/042428, 9 pages, Oct. 26, 2020.

ISA/EP, International Search Report and Written Opinion for International Application No. PCT/US2021/021412, 12 pages, Jun. 9, 2021.

ISA/EP, International Search Report and Written Opinion for International Application No. PCT/US2021/021561, 9 pages, Jun. 28, 2021.

ISA/EP, Partial Search Report and Provisional Opinion for International Application No. PCT/US2020/042427, 13 pages, Oct. 26, 2020.

ISA/EP, Partial Search Report for International Application No. PCT/US2020/033854, 10 pages, Sep. 8, 2020.

"Moving Average Filters", Waybackmachine XP05547422, Retrieved from the Internet: URL:https://web.archive.org/web/20170809081353/https//www.analog.com/media/en/technical-documentation/dsp-book/dsp_book_Ch15.pdf [retrieved on Jan. 24, 2019], Aug. 9, 2017, 1-8.

Office Action for CN App No. 201780029016.7 mailed Mar. 24, 2020, 7 pages.

Office Action for CN App No. 201780029016.7 mailed Sep. 25, 2020, 7 pages.

Office Action for TW App No. 106113266 mailed Jun. 22, 2020, 23 pages.

"Sleep Mode", Wikipedia, Retrieved from the Internet: URL:https://web.archive.org/web/20170908153323/https://en.wikipedia.org/wiki/Sleep_mode [retrieved on Jan. 25, 2019], Sep. 8, 2017, 1-3.

Taiwan Application No. 106114623, 1st Office Action, Dated Aug. 5, 2021, pp. 1-8.

"TMS320C5515 Fingerprint Development Kit (FDK) Hardware Guide", Texas Instruments, Literature No. SPRUFX3, XP055547651, Apr. 2010, 1-26.

Cappelli, et al., "Fingerprint Image Reconstruction from Standard Templates", IEEE Transactions on Pattern Analysis and Machine Intelligence, IEEE Computer Society, vol. 29, No. 9, Sep. 2007, 1489-1503.

Feng, et al., "Fingerprint Reconstruction: From Minutiae to Phase", IEEE Transactions on Pattern Analysis and Machine Intelligence, IEEE Computer Society, vol. 33, No. 2, Feb. 2011, 209-223.

Jiang, et al., "Ultrasonic Fingerprint Sensor with Transmit Beamforming Based on a PMUT Array Bonded to CMOS Circuitry", IEEE Transactions on Ultrasonics Ferroelectrics and Frequency Control, Jan. 1, 2017, 1-9.

Kumar, et al., "Towards Contactless, Low-Cost and Accurate 3D Fingerprint Identification", IEEE Transactions on Pattern Analysis and Machine Intelligence, IEEE Computer Society, vol. 37, No. 3, Mar. 2015, 681-696.

(56) References Cited

OTHER PUBLICATIONS

Pang, et al., "Extracting Valley-Ridge Lines from Point-Cloud-Based 3D Fingerprint Models", IEEE Computer Graphics and Applications, IEEE Service Center, New York, vol. 33, No. 4, Jul./Aug. 2013, 73-81.

Papageorgiou, et al., "Self-Calibration of Ultrasonic Transducers in an Intelligent Data Acquisition System", International Scientific Journal of Computing, 2003, vol. 2, Issue 2 Retrieved Online: URL: https://scholar.google.com/scholar?q=self-calibration+of+ultrasonic+transducers+in+an+intelligent+data+acquisition +system&hl=en&as_sdt=0&as_vis=1&oi=scholart, 2003, 9-15.

Ross, et al., "From Template to Image: Reconstructing Fingerprints from Minutiae Points", IEEE Transactions on Pattern Analysis and Machine Intelligence, IEEE Computer Society, vol. 29, No. 4, Apr. 2007, 544-560.

Tang, et al., "Pulse-echo ultrasonic fingerprint sensor on a chip", 2015 Transducers, 2015 18th International Conference on Solid-State Sensors, Actuators and Microsystems, Apr. 1, 2015, 674-677.

Zhou, et al., "Partial Fingerprint Reconstruction with Improved Smooth Extension", Network and System Security, Springer Berlin Heidelberg, Jun. 3, 2013, 756-762.

ISA/EP, International Search Report and Written Opinion for International Application No. PCT/US2022/075468, 28 pages, Jan. 16, 2023.

Office Action for CN App No. 201780028685.2 mailed Dec. 5, 2022, 11 pages.

Office Action for CN App No. 201780027434.2 mailed Oct. 21, 2022, 10 pages.

Office Action for CN App No. 201780027435.7 mailed Sep. 9, 2022, 9 pages.

Office Action for CN App No. 201780027444.6 mailed Dec. 2, 2022, 17 pages.

Office Action for CN App No. 201780029058.0 mailed Dec. 2, 2022, 9 pages.

Office Action for CN App No. 201780029059.5 mailed Nov. 11, 2022, 11 pages.

Office Action for CN App No. 2020800377355 mailed Aug. 3, 2022, 8 pages.

\* cited by examiner

ANCHOR CONFIGURATIONS FOR AN ARRAY OF ULTRASONIC TRANSDUCERS

RELATED APPLICATIONS

This application claims priority to and the benefit of U.S. Patent Provisional Patent Application 63/260,571, filed on Aug. 25, 2021, entitled "SINGLE AND DUAL LAYER PIEZOELECTRIC ULTRASONIC SENSOR," by Baldasarre et al., and assigned to the assignee of the present application, which is incorporated herein by reference in its entirety.

BACKGROUND

Piezoelectric materials facilitate conversion between mechanical energy and electrical energy. Moreover, a piezoelectric material can generate an electrical signal when subjected to mechanical stress, and can vibrate when subjected to an electrical voltage. Piezoelectric materials are widely utilized in piezoelectric ultrasonic transducers to generate acoustic waves based on an actuation voltage applied to electrodes of the piezoelectric ultrasonic transducer.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

DESCRIPTION OF EMBODIMENTS

Figure 1A:
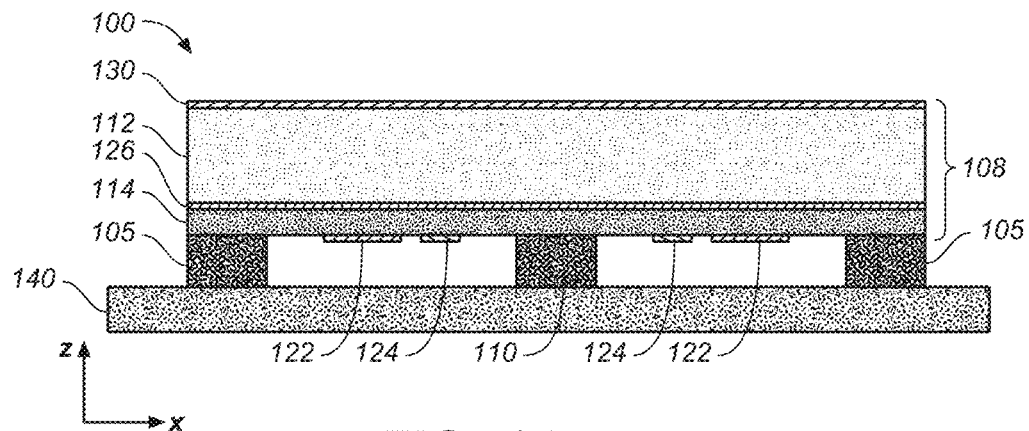
FIG. 1A is a diagram illustrating a side view cross-section of an ultrasonic transducer device with four corner anchors and an inner anchor and with two patterned electrodes placed at the bottom surface of the piezoelectric layer, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "transmitting," "receiving," "sensing," "generating," "imaging," or the like, refer to the actions and processes of an electronic device such as an ultrasonic transducer or an array of ultrasonic transducers.

Embodiments described herein may be discussed in the general context of processor-executable instructions residing on some form of non-transitory processor-readable medium, such as program modules, executed by one or more computers or other devices for controlling operation of one or more dual layer ultrasonic transducer devices. Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more, sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU and a microprocessor, a plurality of microprocessors, one or more microprocessors in conjunction with an SPU core, or any other such configuration.

Overview of Discussion

Discussion includes a description of example anchor configurations for ultrasonic transducer devices including multiple anchors for providing electrical connections to multiple electrodes, in accordance with various embodiments. Example anchor configurations for example ultrasonic transducer devices including multiple external anchors for providing electrical connections to multiple electrodes, according to some embodiments, is then described.

Embodiments described herein provide various anchor configurations for arrays of ultrasonic transducers devices including multiple anchors for providing electrical connections to multiple electrodes. An ultrasonic transducer array includes a substrate, a membrane overlying the substrate, the membrane configured to allow movement at ultrasonic frequencies, and a plurality of anchors connected to the substrate and connected to the membrane. The membrane includes a piezoelectric layer, a plurality of first electrodes, and a plurality of second electrodes, wherein each ultrasonic transducer of a plurality of ultrasonic transducers includes at least a first electrode and at least a second electrode. The plurality of anchors defines a cavity between the substrate and the membrane. The plurality of anchors includes a first anchor including a first electrical connection for electrically coupling at least one first electrode to control circuitry for controlling the at least one first electrode during a transmit operation and a second anchor including a second electrical connection for electrically coupling at least one second electrode to the control circuitry for controlling the at least one second electrode during a receive operation. According to various embodiments, the membrane further includes a structural layer.

In some embodiments, the ultrasonic transducer array is a two-dimensional array of ultrasonic transducers. In some embodiments, the plurality of anchors includes corner anchors located at corners of the plurality of ultrasonic transducers such that a corner anchor is shared by four ultrasonic transducers of the plurality of ultrasonic transducers. In some embodiments, the plurality of anchors includes side anchors located at sides of the plurality of ultrasonic transducers such that a side anchor is shared by two ultrasonic transducers of the plurality of ultrasonic transducers. In some embodiments, the plurality of anchors includes inner anchors located within an ultrasonic transducer of the plurality of ultrasonic transducers such that an inner anchor is dedicated to one ultrasonic transducer of the plurality of ultrasonic transducers.

In other embodiments, the ultrasonic transducer array is a one-dimensional array of ultrasonic transducers. In some embodiments, the plurality of anchors includes shared side anchors located at shared sides of the plurality of ultrasonic transducers such that a shared side anchor is shared by two ultrasonic transducers of the plurality of ultrasonic transducers. In some embodiments, the plurality of anchors includes exclusive side anchors located at exclusive sides of the plurality of ultrasonic transducers such that an exclusive side is a side that is not shared by any ultrasonic transducers of the plurality of ultrasonic transducers. In some embodiments, the plurality of anchors includes corner anchors located at corners of the plurality of ultrasonic transducers such that a corner anchor is shared by two ultrasonic transducers of the plurality of ultrasonic transducers, where a corner anchor is on a shared side of the ultrasonic transducer and an exclusive side of the ultrasonic transducer. In some embodiments, the plurality of anchors includes inner anchors located within an ultrasonic transducer of the plurality of ultrasonic transducers such that an inner anchor is dedicated to one ultrasonic transducer of the plurality of ultrasonic transducers.

The described ultrasonic transducer devices can be used for generation of acoustic signals or measurement of acoustically sensed data in various applications, such as, but not limited to, medical applications, security systems, biometric systems (e.g., fingerprint sensors and/or motion/gesture recognition sensors), mobile communication systems, industrial automation systems, consumer electronic devices, robotics, etc., for example, using multiple ultrasonic transducer devices operating collectively in one-dimensional or two-dimensional arrays.

Embodiments described herein provide arrays of ultrasonic transducer devices, where the ultrasonic transducer devices have multiple anchors for providing multiple connections to multiple electrodes. One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

Embodiments described herein provide different anchor configurations for arrays of ultrasonic transducer devices (e.g., one-dimensional arrays and two-dimensional arrays).

The described ultrasonic transducer devices (e.g., ultrasonic transducer device 100) are capable of generating and receiving ultrasonic signals. An object in a path of the generated ultrasonic signals can create a disturbance (e.g., changes in frequency or phase, reflection signal, echoes, etc.) that can then be sensed. The interference can be analyzed to determine physical parameters such as (but not limited to) distance, density and/or speed of the object. As an example, the ultrasonic transducer devices can be utilized in various applications, such as, but not limited to, fingerprint or physiologic sensors suitable for wireless devices, industrial systems, automotive systems, robotics, telecommunications, security, medical devices, etc. For example, the ultrasonic transducer devices can be part of a sensor array comprising a plurality of ultrasonic transducers deposited on a wafer, along with various logic, control and communication electronics. A sensor array may comprise homogenous or identical ultrasonic transducer devices, or a number of different or heterogonous device structures.

In various embodiments, the ultrasonic transducer devices employ a piezoelectric layer (e.g., piezoelectric layer 114), comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production (transmitting) and sensing (receiving). The piezoelectric layer can generate electric charges under mechanical stress and conversely experience a mechanical strain in the presence of an electric field. For example, the piezoelectric layer can sense mechanical vibrations caused by an ultrasonic signal and produce an electrical charge at the frequency (e.g., ultrasonic frequency) of the vibrations. Additionally, the piezoelectric layer can generate an ultrasonic wave by vibrating in an oscillatory fashion that might be at the same frequency (e.g., ultrasonic frequency) as an input current generated by an alternating current (AC) voltage applied across the piezoelectric layer. It should be appreciated that piezoelectric layer can include almost any material (or combination of materials) that exhibits piezoelectric properties. The polarization is directly proportional to the applied stress and is direction dependent so that compressive and tensile stresses results in electric fields of opposite polarizations.

It should be appreciated that, ultrasonic transducer devices described herein can be one of many types of geometric shapes (e.g., ring, circle, square, octagon, hexagon, etc.). For example, a sensing device may include a two-dimensional array of ultrasonic transducer devices. In some embodiments, ultrasonic transducer devices can be of a shape that allows for close placement of ultrasonic transducer devices. While the ultrasonic transducer devices described herein are square and rectangular in shape, it should be appreciated that the principles described herein allow for the use of ultrasonic transducer devices of different shapes, such as triangular and hexagon shaped ultrasonic transducer devices with different numbers of corner anchors per ultrasonic transducer device.

Ultrasonic Transducer Devices Including Multiple Anchors Providing Electrical Connections to Multiple Electrodes FIG. 1A is a diagram illustrating a side view cross-section (indicated at line 102 of FIG. 1B) of an ultrasonic transducer device 100 with four corner anchors 105 and an inner anchor 110 and with two patterned electrodes 122 and 124 placed at the bottom surface of the piezoelectric layer 114, according to some embodiments. In some embodiments, ultrasonic transducer device 100 is a piezoelectric micromachined ultrasonic transducer (PMUT) device. Ultrasonic transducer device 100 is one ultrasonic transducer of a two-dimensional array of ultrasonic transducer devices 100, where each ultrasonic transducer includes a pair of electrodes 122 and 124. Corner anchors 105 are positioned at a corner of ultrasonic transducer device 100 and inner anchor 110 is positioned inside of ultrasonic transducer device 100. It should be appreciated that corner anchors 105 are shared by adjacent ultrasonic transducer devices 100 (e.g., four ultrasonic transducer devices 100 share one corner anchor 105) and that inner anchor 110 is dedicated to one ultrasonic transducer device 100.

Ultrasonic transducer device 100 includes a membrane 108 overlying and attached to four corner anchors 105 and an inner anchor 110. It should be appreciated that membrane 108 spans all ultrasonic transducer devices 100 of the two-dimensional array of ultrasonic transducer devices 100. Corner anchors 105 and inner anchor 110 may be made of electrically conducting materials, such as and without limitation, aluminum, molybdenum, or titanium. In some embodiments, corner anchors 105 and inner anchor 110 may be made of dielectric materials, such as silicon dioxide, silicon nitride or aluminum oxide that have electrical connections along the sides or in vias through corner anchors 105 and inner anchor 110, for electrically coupling electrodes 122, 124, and/or 126 to electrical wiring in substrate 140. For example, substrate 140 may include terminals for electrically coupling electrodes 122, 124, and/or 126 to control circuitry.

In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to corner anchors 105 and inner anchor 110. Membrane 108 includes a piezoelectric layer 114 and electrodes 122, 124, and 126, with electrodes 122 and 124 on the same side of piezoelectric layer 114 and electrodes 126 on the opposite side of piezoelectric layer 114 than electrodes 122 and 124. In accordance with some embodiments, membrane 108 further includes structural layer 112 (e.g., a stiffening layer or a mechanical support layer) to mechanically stiffen membrane 108. In various embodiments, structural layer 112 may include at least one of, and without limitation, silicon, silicon oxide, silicon nitride, aluminum, molybdenum, titanium, etc. In some embodiments, membrane 108 also includes ground electrode 130 placed at the opposite side of the cavity. It should be appreciated that in accordance with various embodiments, membrane 108 can also include other layers (not shown), such as an acoustic coupling layer. The acoustic coupling layer is for supporting transmission of acoustic signals, and, if present, is above membrane 108. It should be appreciated that acoustic coupling layer can include air, liquid, gel-like materials, or other materials for supporting transmission of acoustic signals.

Figure 1B:
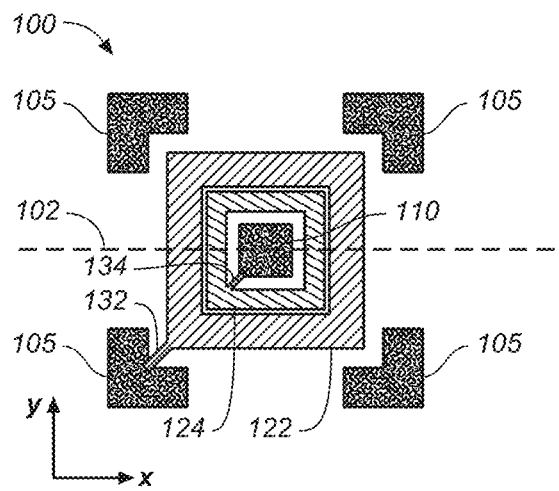
FIG. 1B is a diagram illustrating a top view of the electrode layout of an ultrasonic transducer device with four corner anchors and an inner anchor and with two patterned electrodes placed at the bottom surface of the piezoelectric layer, according to some embodiments.

FIG. 1B is a diagram illustrating a top view of the electrode layout of an ultrasonic transducer device 100 with four corner anchors 105 and an inner anchor 110 and with two patterned electrodes 122 and 124 placed at the bottom surface of the piezoelectric layer 114, according to some embodiments. In the illustrated embodiment, one corner anchor 105 is connected to an electric connector 132 for connecting to electrode 122 to an electrical potential and inner anchor 110 is connected to an electric connector 134 for connecting to electrode 124 to an electrical potential.

Figure 1C:
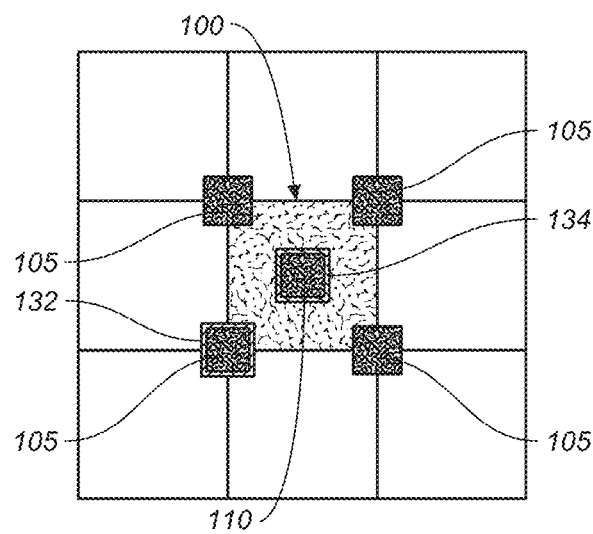
FIG. 1C is a diagram illustrating a top view of the anchor configuration of a two-dimensional array of ultrasonic transducer devices with four corner anchors and an inner anchor, according to some embodiments.

In some embodiments, a plurality of ultrasonic transducer devices 100 are comprised within a two-dimensional (or one-dimensional) array of ultrasonic transducer devices 100. FIG. 1C is a diagram illustrating a top view of the anchor configuration of a two-dimensional array of ultrasonic transducer devices 100 with four corner anchors 105 and an inner anchor 110 per ultrasonic transducer device 100, according to some embodiments. It should be appreciated that FIG. 1C shows the anchor configuration for one ultrasonic transducer device 100 surrounded by other ultrasonic transducer devices 100 for which the anchor configuration is not shown apart from sharing corner anchors 105.

In some embodiments, the array of ultrasonic transducer devices 100 may be coupled to a platen layer above an acoustic coupling layer for containing the acoustic coupling layer and providing a contact surface for a finger or other sensed object with the array of ultrasonic transducer devices 100. It should be appreciated that, in various embodiments, the acoustic coupling layer provides a contact surface, such that a platen layer is optional. It should be appreciated that the contact surface can be flat or of a varying thickness (e.g., curved).

Further, ultrasonic transducer device 100 comprises electrodes 122, 124, and 126 that supply and/or collect the electrical charge to/from piezoelectric layer 114. Electrodes 122, 124, and 126 can be connected to substrate 140 or the underlying circuitry via one or more terminals on substrate 140. In some embodiments, ground electrode 130 can be connected to substrate 140 or the underlying circuitry via one or more terminals on substrate 140. In the illustrated embodiment, one corner anchor 105 is connected to an electric connector 132 for connecting to electrode 122 to an electrical potential and inner anchor 110 is connected to an electric connector 134 for connecting to electrode 124 to an electrical potential. Depending on the mode of operation, two or more electrodes may share a single terminal. It should be appreciated that electrodes 122 and 124 are patterned electrodes (e.g., a patterned layer). As an example, electrodes 122, 124, 126, and 130 can be comprised of almost any metal layers, such as, but not limited to, aluminum (Al), titanium (Ti), Molybdenum (Mo), etc.

In accordance with various embodiments, electrodes 122, 124, and/or 126 can be patterned in particular shapes (e.g., ring, circle, square, octagon, hexagon, etc.) that are coupled with the membrane 108. In some embodiments, electrodes 122 and 124 are coupled to different terminals and operate as separate electrodes, where electrode 126 is coupled to ground (GND) or other potential. In some embodiments, electrodes 130 and 126 are coupled to ground (GND). In accordance with some embodiments, electrode 122 is dedicated for use in a transmit operation for generating an ultrasonic signal and electrode 124 is dedicated for use in a receive operation for receiving a reflected ultrasonic signal.

Figure 2A:
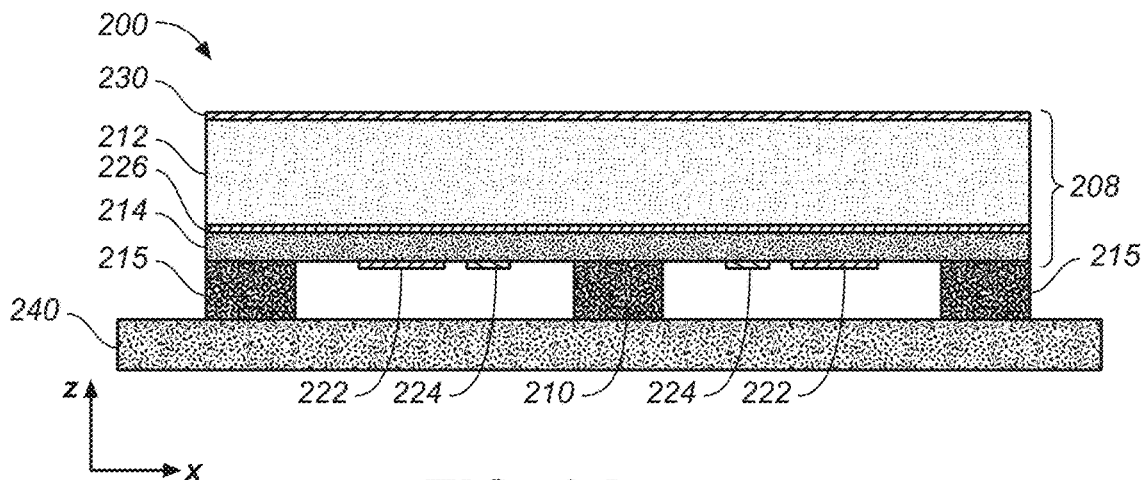
FIG. 2A is a diagram illustrating a side view cross-section of an ultrasonic transducer device with two side anchors and an inner anchor and with two patterned electrodes placed at the bottom surface of the piezoelectric layer, according to some embodiments.

FIG. 2A is a diagram illustrating a side view cross-section (indicated at line 202 of FIG. 2B) of an ultrasonic transducer device 200 with two side anchors 215 and an inner anchor 210 and with two patterned electrodes 222 and 224 placed at the bottom surface of the piezoelectric layer 214, according to some embodiments. In some embodiments, ultrasonic transducer device 200 is a PMUT device. Ultrasonic transducer device 200 is one ultrasonic transducer of a two-dimensional array of ultrasonic transducer devices 200, where each ultrasonic transducer includes a pair of electrodes 222 and 224. Side anchors 215 are positioned at a side of ultrasonic transducer device 200 and inner anchor 210 is positioned inside of ultrasonic transducer device 200. It should be appreciated that side anchors 215 are shared by adjacent ultrasonic transducer devices 200 (e.g., two ultrasonic transducer devices 200 share one side anchor 215) and that inner anchor 210 is dedicated to one ultrasonic transducer device 200.

Ultrasonic transducer device 200 includes a membrane 208 overlying and attached to two side anchors 215 and an inner anchor 210. It should be appreciated that membrane 208 spans all ultrasonic transducer devices 200 of the two-dimensional array of ultrasonic transducer devices 200. Side anchors 215 and inner anchor 210 may be made of electrically conducting materials, such as and without limitation, aluminum, molybdenum, or titanium. In some embodiments, side anchors 215 and inner anchor 210 may be made of dielectric materials, such as silicon dioxide, silicon nitride or aluminum oxide that have electrical connections along the sides or in vias through side anchors 215 and inner anchor 210, for electrically coupling electrodes 222, 224, and/or 226 to electrical wiring in substrate 240. For example, substrate 240 may include terminals for electrically coupling electrodes 222, 224, and/or 226 to control circuitry.

In various embodiments, substrate 240 may include at least one of, and without limitation, silicon or silicon nitride. It should be appreciated that substrate 240 may include electrical wirings and connection, such as aluminum or copper. In one embodiment, substrate 240 includes a CMOS logic wafer bonded to side anchors 215 and an inner anchor 210. Membrane 208 includes piezoelectric layer 214 and electrodes 222, 224, and 226, with electrodes 222 and 224 on the same side of piezoelectric layer 214 and electrodes 226 on the opposite side of piezoelectric layer 214 than electrodes 222 and 224. In some embodiments, membrane 208 further comprises electrode 230 connected to ground. In accordance with some embodiments, membrane 208 further includes structural layer 212 (e.g., a stiffening layer or a mechanical support layer) to mechanically stiffen membrane 208. In various embodiments, structural layer 212 may include at least one of, and without limitation, silicon, silicon oxide, silicon nitride, aluminum, molybdenum, titanium, etc. It should be appreciated that in accordance with various embodiments, membrane 208 can also include other layers (not shown), such as an acoustic coupling layer. The acoustic coupling layer is for supporting transmission of acoustic signals, and, if present, is above membrane 208. It should be appreciated that acoustic coupling layer can include air, liquid, gel-like materials, or other materials for supporting transmission of acoustic signals.

Figure 2B:
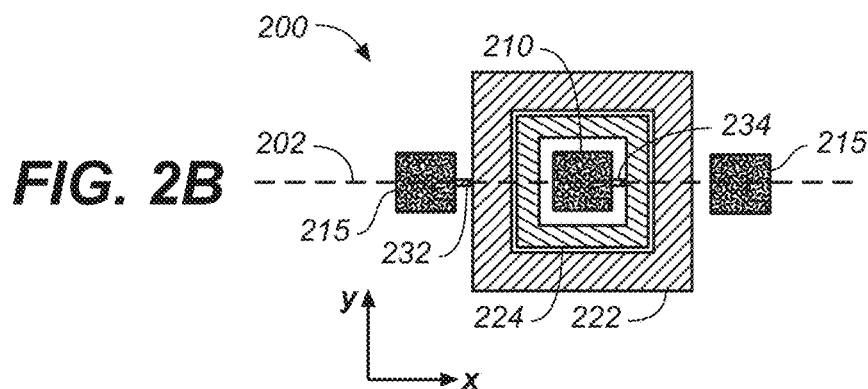
FIG. 2B is a diagram illustrating a top view of the electrode layout of an ultrasonic transducer device with two side anchors and an inner anchor and with two patterned electrodes placed at the bottom surface of the piezoelectric layer, according to some embodiments.

FIG. 2B is a diagram illustrating a top view of the electrode layout of an ultrasonic transducer device 200 with two side anchors 215 and an inner anchor 210 and with two patterned electrodes 222 and 224 placed at the bottom surface of the piezoelectric layer 214, according to some embodiments. In the illustrated embodiment, one side anchor 215 is connected to an electric connector 232 for connecting to electrode 222 to an electrical potential and inner anchor 210 is connected to an electric connector 234 for connecting to electrode 224 to an electrical potential.

Figure 2C:
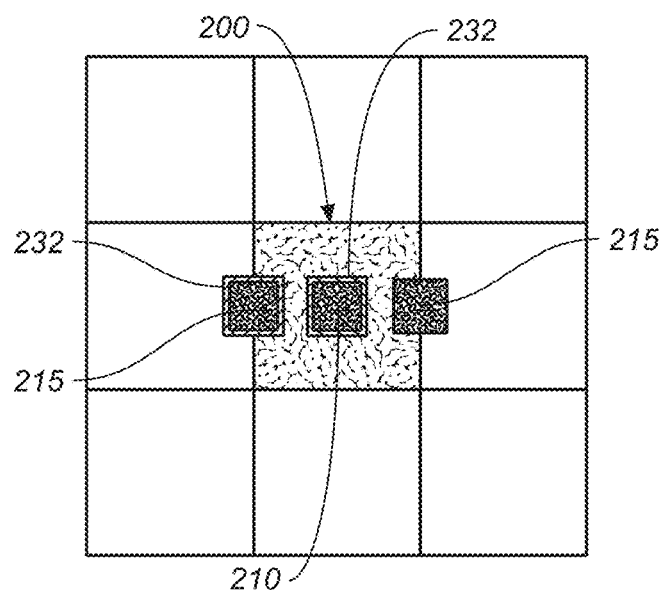
FIG. 2C is a diagram illustrating a top view of the anchor configuration of a two-dimensional array of ultrasonic transducer devices with two side anchors and an inner anchor, according to some embodiments.

In some embodiments, a plurality of ultrasonic transducer devices 200 are comprised within a two-dimensional (or one-dimensional) array of ultrasonic transducer devices 200. FIG. 2C is a diagram illustrating a top view of the anchor configuration of a two-dimensional array of ultrasonic transducer devices 200 with two side anchors 215 and an inner anchor 210 per ultrasonic transducer device 200, according to some embodiments. It should be appreciated that FIG. 2C shows the anchor configuration for one ultrasonic transducer device 200 surrounded by other ultrasonic transducer devices 200 for which the anchor configuration is not shown apart from sharing side anchors 215.

In some embodiments, the array of ultrasonic transducer devices 200 may be coupled to a platen layer above an acoustic coupling layer for containing the acoustic coupling layer and providing a contact surface for a finger or other sensed object with the array of ultrasonic transducer devices 200. It should be appreciated that, in various embodiments, the acoustic coupling layer provides a contact surface, such that a platen layer is optional. It should be appreciated that the contact surface can be flat or of a varying thickness (e.g., curved).

Further, ultrasonic transducer device 200 comprises electrodes 222, 224, and 226 that supply and/or collect the electrical charge to/from piezoelectric layer 214. Electrodes 222, 224, and 226 can be connected to substrate 240 or the underlying circuitry via one or more terminals on substrate 240. In some embodiments, ground electrode 230 can be connected to substrate 240 or the underlying circuitry via one or more terminals on substrate 240. In the illustrated embodiment, one side anchor 215 is connected to an electric connector 232 for connecting to electrode 222 to an electrical potential and inner anchor 210 is connected to an electric connector 234 for connecting to electrode 224 to an electrical potential. Depending on the mode of operation, two or more electrodes may share a single terminal. It should be appreciated that electrodes 222 and 224 are patterned electrodes (e.g., a patterned layer). As an example, electrodes 222, 224, 226, and 230 can be comprised of almost any metal layers, such as, but not limited to, aluminum (Al), titanium (Ti), Molybdenum (Mo), etc.

In accordance with various embodiments, electrodes 222, 224, and/or 226 can be patterned in particular shapes (e.g., ring, circle, square, octagon, hexagon, etc.) that are coupled with the membrane 208. In some embodiments, electrodes 222 and 224 are coupled to different terminals and operate as separate electrodes, where electrode 226 is coupled to ground (GND) or other potential. In some embodiments, electrodes 230 and 226 are coupled to ground (GND). In accordance with some embodiments, electrode 222 is dedicated for use in a transmit operation for generating an ultrasonic signal and electrode 224 is dedicated for use in a receive operation for receiving a reflected ultrasonic signal.

Figure 3A:
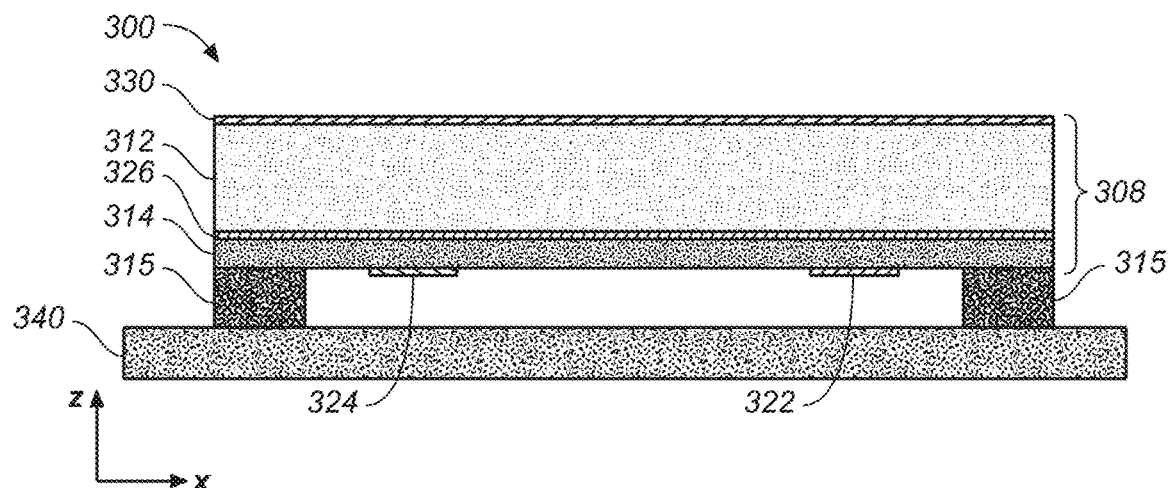
FIG. 3A is a diagram illustrating a side view cross-section of an ultrasonic transducer device with four corner anchors and two side anchors and with two patterned electrodes placed at the bottom surface of the piezoelectric layer, according to some embodiments.

FIG. 3A is a diagram illustrating a side view cross-section (indicated at line 302 of FIG. 3B) of an ultrasonic transducer device 300 with two side anchors 315 and four corner anchors 305 (illustrated in FIG. 3B), and with two patterned electrodes 322 and 324 placed at the bottom surface of the piezoelectric layer 314, according to some embodiments. In some embodiments, ultrasonic transducer device 300 is a PMUT device. Ultrasonic transduce device 300 is one ultrasonic transducer of a two-dimensional array of ultrasonic transducer devices 300, where each ultrasonic transducer includes a pair of electrodes 322 and 324. Side anchors 315 are positioned at a side of ultrasonic transducer device 300 and corner anchors 305 are positioned at a corner of ultrasonic transducer device 300. It should be appreciated that side anchors 315 and corner anchors 305 are shared by adjacent ultrasonic transducer devices 300 (e.g., two ultrasonic transducer devices 300 share one side anchor 315 and four ultrasonic transducer devices 300 share one corner anchor 305).

Ultrasonic transducer device 300 includes a membrane 308 overlying and attached to two side anchors 315 and four corner anchors 305. It should be appreciated that membrane 308 spans all ultrasonic transducer devices 300 of the two-dimensional array of ultrasonic transducer devices 300. Side anchors 315 and corner anchors 305 may be made of electrically conducting materials, such as and without limitation, aluminum, molybdenum, or titanium. In some embodiments, side anchors 315 and corner anchors 305 may be made of dielectric materials, such as silicon dioxide, silicon nitride or aluminum oxide that have electrical connections along the sides or in vias through side anchors 315 and corner anchors 305, for electrically coupling electrodes 322, 324, and/or 326 to electrical wiring in substrate 340. For example, substrate 340 may include terminals for electrically coupling electrodes 322, 324, and/or 326 to control circuitry.

In various embodiments, substrate 340 may include at least one of, and without limitation, silicon or silicon nitride. It should be appreciated that substrate 340 may include electrical wirings and connection, such as aluminum or copper. In one embodiment, substrate 340 includes a CMOS logic wafer bonded to side anchors 315 and corner anchors 305. Membrane 308 includes a piezoelectric layer 314 and electrodes 322, 324, and 326, with electrodes 322 and 324 on the same side of piezoelectric layer 314 and electrodes 326 on the opposite side of piezoelectric layer 314 than electrodes 322 and 324. In some embodiments, membrane 308 further includes electrode 330 connected to ground. In accordance with some embodiments, membrane 308 further includes structural layer 312 (e.g., a stiffening layer or a mechanical support layer) to mechanically stiffen membrane 308. In various embodiments, structural layer 312 may include at least one of, and without limitation, silicon, silicon oxide, silicon nitride, aluminum, molybdenum, titanium, etc. It should be appreciated that in accordance with various embodiments, membrane 308 can also include other layers (not shown), such as an acoustic coupling layer. The acoustic coupling layer is for supporting transmission of acoustic signals, and, if present, is above membrane 308. It should be appreciated that acoustic coupling layer can include air, liquid, gel-like materials, or other materials for supporting transmission of acoustic signals.

Figure 3B:
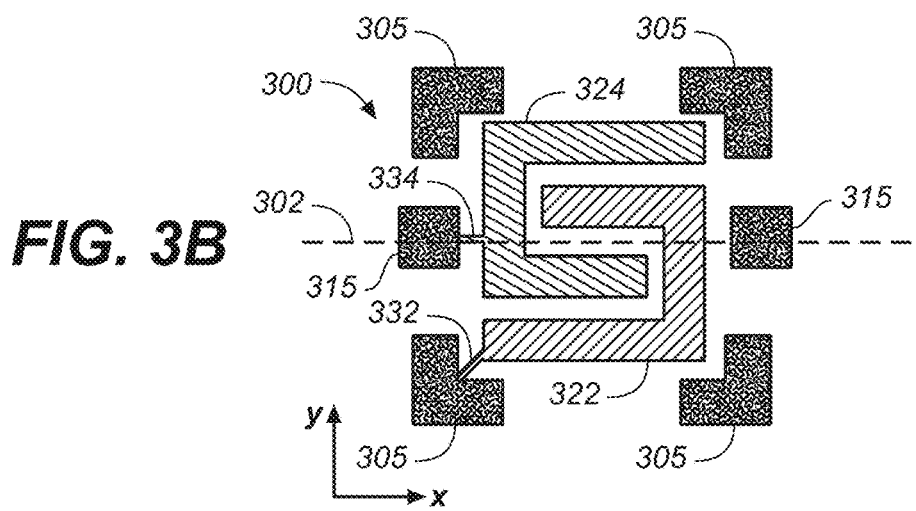
FIG. 3B is a diagram illustrating a top view of the electrode layout of an ultrasonic transducer device with four corner anchors and two side anchors and with two patterned electrodes placed at the bottom surface of the piezoelectric layer, according to some embodiments.

FIG. 3B is a diagram illustrating a top view of the electrode layout of an ultrasonic transducer device 300 with two side anchors 315 and four corner anchors 305 and with two patterned electrodes 322 and 324 placed at the bottom surface of the piezoelectric layer 314, according to some embodiments. In the illustrated embodiment, one side anchor 315 is connected to an electric connector 334 for connecting to electrode 324 to an electrical potential and one corner anchor 305 is connected to an electric connector 332 for connecting to electrode 322 to an electrical potential.

Figure 3C:
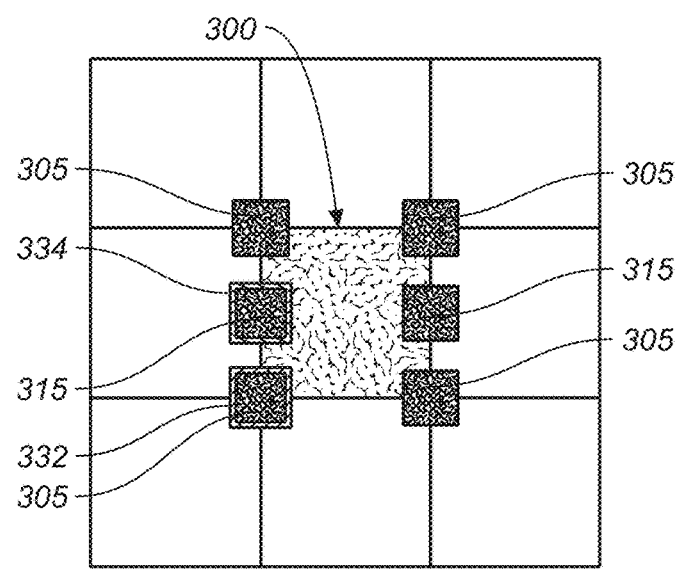
FIG. 3C is a diagram illustrating a top view of the anchor configuration of a two-dimensional array of ultrasonic transducer devices with four corner anchors and two side anchors, according to some embodiments.

In some embodiments, a plurality of ultrasonic transducer devices 300 are comprised within a two-dimensional (or one-dimensional) array of ultrasonic transducer devices 300. FIG. 3C is a diagram illustrating a top view of the anchor configuration of a two-dimensional array of ultrasonic transducer devices 300 with two side anchors 315 and four corner anchors 305 per ultrasonic transducer device 300, according to some embodiments. It should be appreciated that FIG. 3C shows the anchor configuration for one ultrasonic transducer device 300 surrounded by other ultrasonic transducer devices 300 for which the anchor configuration is not shown apart from sharing side anchors 315 and corner anchors 305.

In some embodiments, the array of ultrasonic transducer devices 300 may be coupled to a platen layer above an acoustic coupling layer for containing the acoustic coupling layer and providing a contact surface for a finger or other sensed object with the array of ultrasonic transducer devices 300. It should be appreciated that, in various embodiments, the acoustic coupling layer provides a contact surface, such that a platen layer is optional. It should be appreciated that the contact surface can be flat or of a varying thickness (e.g., curved).

Further, ultrasonic transducer device 300 comprises electrodes 322, 324, and 326 that supply and/or collect the electrical charge to/from piezoelectric layer 314. Electrodes 322, 324, and 326 can be connected to substrate 340 or the underlying circuitry via one or more terminals on substrate 340. In some embodiments, ground electrode 330 can be connected to substrate 340 or the underlying circuitry via one or more terminals on substrate 340. In the illustrated embodiment, one side anchor 315 is connected to an electric connector 334 for connecting to electrode 324 to an electrical potential and one corner anchor 305 is connected to an electric connector 332 for connecting to electrode 322 to an electrical potential. Depending on the mode of operation, two or more electrodes may share a single terminal. It should be appreciated that electrodes 322 and 324 are patterned electrodes (e.g., a patterned layer). As an example, electrodes 322, 324, 326, and 330 can be comprised of almost any metal layers, such as, but not limited to, aluminum (Al), titanium (Ti), Molybdenum (Mo), etc.

In accordance with various embodiments, electrodes 322, 324, and/or 326 can be patterned in particular shapes (e.g., ring, circle, square, octagon, hexagon, etc.) that are coupled with the membrane 308. In some embodiments, electrodes 322 and 324 are coupled to different terminals and operate as separate electrodes, where electrode 326 is coupled to ground (GND) or other potential. In some embodiments, electrodes 330 and 326 are coupled to ground (GND). In accordance with some embodiments, electrode 322 is dedicated for use in a transmit operation for generating an ultrasonic signal and electrode 324 is dedicated for use in a receive operation for receiving a reflected ultrasonic signal.

Figure 4A:
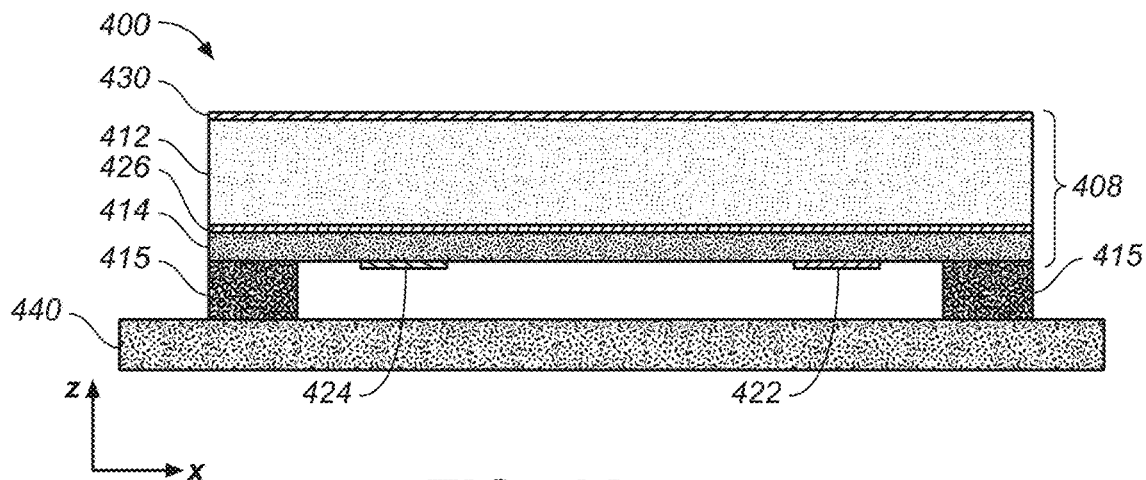
FIG. 4A is a diagram illustrating a side view cross-section of an ultrasonic transducer device with four side anchors and with two patterned electrodes placed at the bottom surface of the piezoelectric layer, according to some embodiments.

FIG. 4A is a diagram illustrating a side view cross-section (indicated at line 402 of FIG. 4B) of an ultrasonic transducer device 400 with four side anchors 415 and with two patterned electrodes 422 and 424 placed at the bottom surface of the piezoelectric layer 414, according to some embodiments. In some embodiments, ultrasonic transducer device 400 is a PMUT device. Ultrasonic transducer device 400 is one ultrasonic transducer of a two-dimensional array of ultrasonic transducer devices 400, where each ultrasonic transducer includes a pair of electrodes 422 and 424. Side anchors 415 are positioned at a side of ultrasonic transducer device 400. It should be appreciated that side anchors 415 are shared by adjacent ultrasonic transducer devices 400 (e.g., two ultrasonic transducer devices 400 share one side anchor 415).

Ultrasonic transducer device 400 includes a membrane 408 overlying and attached to four side anchors 415. It should be appreciated that membrane 408 spans all ultrasonic transducer devices 400 of the two-dimensional array of ultrasonic transducer devices 400. Side anchors 415 may be made of electrically conducting materials, such as and without limitation, aluminum, molybdenum, or titanium. In some embodiments, side anchors 415 may be made of dielectric materials, such as silicon dioxide, silicon nitride or aluminum oxide that have electrical connections along the sides or in vias through side anchors 415, for electrically coupling electrodes 422, 424, and/or 426 to electrical wiring in substrate 440. For example, substrate 440 may include terminals for electrically coupling electrodes 422, 424, and/or 426 to control circuitry.

In various embodiments, substrate 440 may include at least one of, and without limitation, silicon or silicon nitride. It should be appreciated that substrate 440 may include electrical wirings and connection, such as aluminum or copper. In one embodiment, substrate 440 includes a CMOS logic wafer bonded to side anchors 415. Membrane 408 includes piezoelectric layer 414 and electrodes 422, 424, and 426, with electrodes 422 and 424 on the same side of piezoelectric layer 414 and electrodes 426 on the opposite side of piezoelectric layer 414 than electrodes 422 and 424. In some embodiments, membrane 308 further includes electrode 430 connected to ground. In accordance with some embodiments, membrane 408 further includes structural layer 412 (e.g., a stiffening layer or a mechanical support layer) to mechanically stiffen membrane 408. In various embodiments, structural layer 412 may include at least one of, and without limitation, silicon, silicon oxide, silicon nitride, aluminum, molybdenum, titanium, etc. It should be appreciated that in accordance with various embodiments, membrane 408 can also include other layers (not shown), such as an acoustic coupling layer. The acoustic coupling layer is for supporting transmission of acoustic signals, and, if present, is above membrane 408. It should be appreciated that acoustic coupling layer can include air, liquid, gel-like materials, or other materials for supporting transmission of acoustic signals.

Figure 4B:
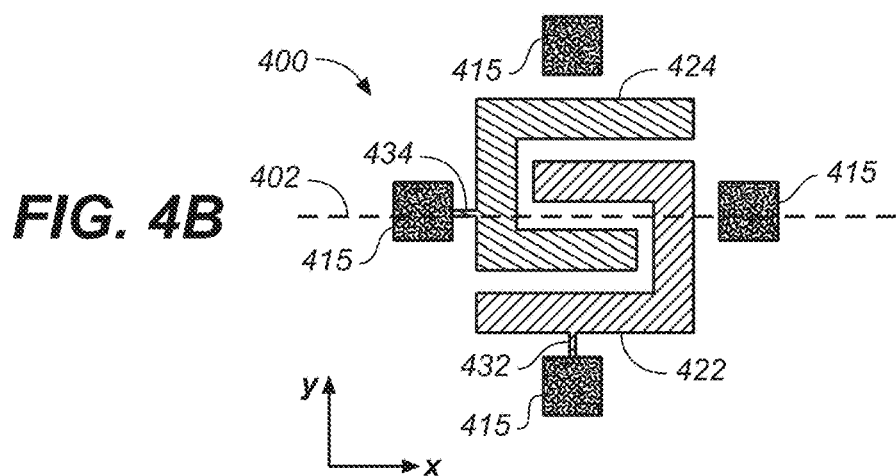
FIG. 4B is a diagram illustrating a top view of the electrode layout of an ultrasonic transducer device with four side anchors and with two patterned electrodes placed at the bottom surface of the piezoelectric layer, according to some embodiments.

FIG. 4B is a diagram illustrating a top view of the electrode layout of an ultrasonic transducer device 400 with four side anchors 415 and with two patterned electrodes 422 and 424 placed at the bottom surface of the piezoelectric layer 414, according to some embodiments. In the illustrated embodiment, one side anchor 415 is connected to an electric connector 432 for connecting to electrode 422 to an electrical potential and another side anchor 415 is connected to an electric connector 434 for connecting to electrode 424 to an electrical potential.

Figure 4C:
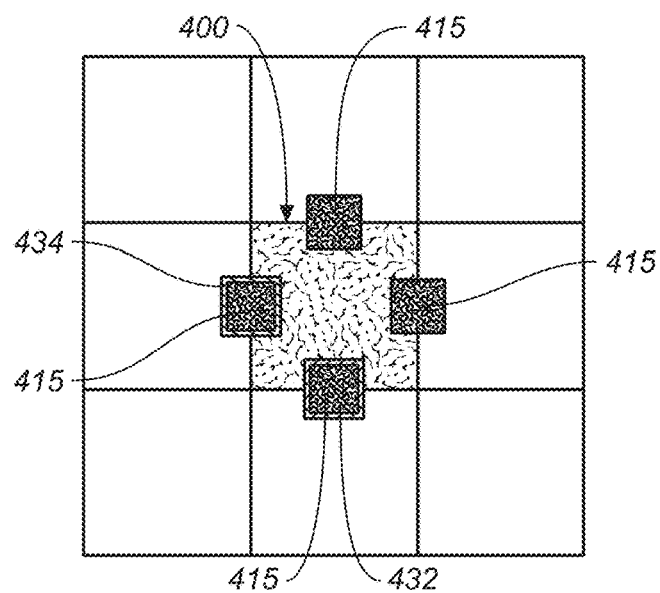
FIG. 4C is a diagram illustrating a top view of the anchor configuration of a two-dimensional array of ultrasonic transducer devices with four side anchors, according to some embodiments.

In some embodiments, a plurality of ultrasonic transducer devices 400 are comprised within a two-dimensional (or one-dimensional) array of ultrasonic transducer devices 400. FIG. 4C is a diagram illustrating a top view of the anchor configuration of a two-dimensional array of ultrasonic transducer devices 400 with four side anchors 415 per ultrasonic transducer device 400, according to some embodiments. It should be appreciated that FIG. 4C shows the anchor configuration for one ultrasonic transducer device 400 surrounded by other ultrasonic transducer devices 400 for which the anchor configuration is not shown apart from sharing side anchors 415.

In some embodiments, the array of ultrasonic transducer devices 400 may be coupled to a platen layer above an acoustic coupling layer for containing the acoustic coupling layer and providing a contact surface for a finger or other sensed object with the array of ultrasonic transducer devices 400. It should be appreciated that, in various embodiments, the acoustic coupling layer provides a contact surface, such that a platen layer is optional. It should be appreciated that the contact surface can be flat or of a varying thickness (e.g., curved).

Further, ultrasonic transducer device 400 comprises electrodes 422, 424, and 426 that supply and/or collect the electrical charge to/from piezoelectric layer 414. Electrodes 422, 424, and 426 can be connected to substrate 440 or the underlying circuitry via one or more terminals on substrate 440. In some embodiments, ground electrode 430 can be connected to substrate 440 or the underlying circuitry via one or more terminals on substrate 440. In the illustrated embodiment, one side anchor 415 is connected to an electric connector 432 for connecting to electrode 422 to an electrical potential and another side anchor 415 is connected to an electric connector 434 for connecting to electrode 424 to an electrical potential. Depending on the mode of operation, two or more electrodes may share a single terminal. It should be appreciated that electrodes 422 and 424 are patterned electrodes (e.g., a patterned layer). As an example, electrodes 422, 424, 426, and 430 can be comprised of almost any metal layers, such as, but not limited to, aluminum (Al), titanium (Ti), Molybdenum (Mo), etc.

In accordance with various embodiments, electrodes 422, 424, and/or 426 can be patterned in particular shapes (e.g., ring, circle, square, octagon, hexagon, etc.) that are coupled with the membrane 408. In some embodiments, electrodes 422 and 424 are coupled to different terminals and operate as separate electrodes, where electrode 426 is coupled to ground (GND) or other potential. In some embodiments, electrodes 430 and 426 are coupled to ground (GND). In accordance with some embodiments, electrode 422 is dedicated for use in a transmit operation for generating an ultrasonic signal and electrode 424 is dedicated for use in a receive operation for receiving a reflected ultrasonic signal.

Figure 5A:
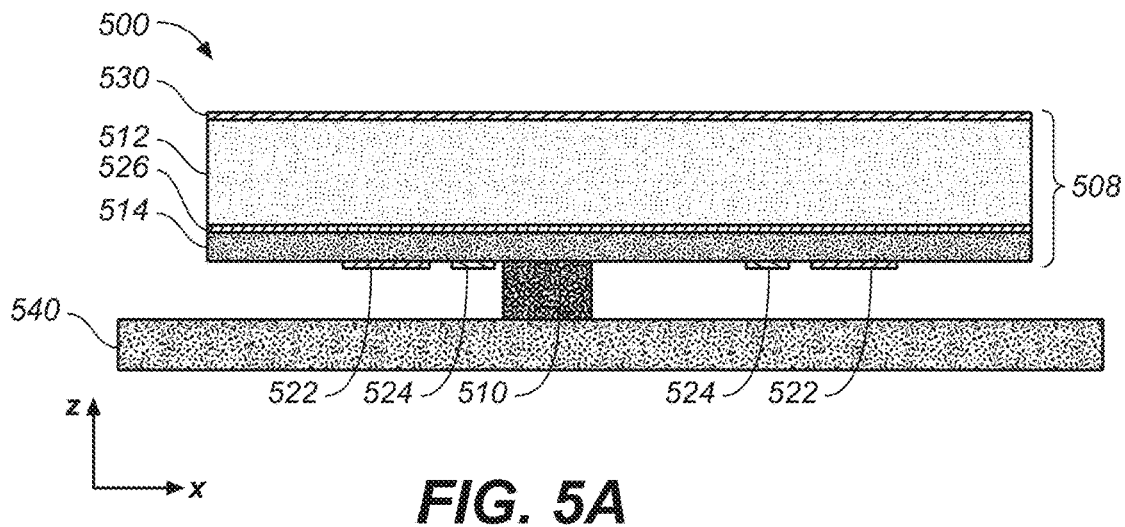
FIG. 5A is a diagram illustrating a side view cross-section of an ultrasonic transducer device with two inner anchors and with two patterned electrodes placed at the bottom surface of the piezoelectric layer, according to some embodiments.

FIG. 5A is a diagram illustrating a side view cross-section (indicated at line 502 of FIG. 5B) of an ultrasonic transducer device 500 with two inner anchors 510 and with two patterned electrodes 522 and 524 placed at the bottom surface of the piezoelectric layer 514, according to some embodiments. In some embodiments, ultrasonic transducer device 500 is a PMUT device. Ultrasonic transducer device 500 is one ultrasonic transducer of a two-dimensional array of ultrasonic transducer devices 500, where each ultrasonic transducer includes a pair of electrodes 522 and 524. Inner anchors 510 are positioned inside of ultrasonic transducer device 500. It should be appreciated that inner anchors 510 are dedicated to ultrasonic transducer device 500 and are not shared by any adjacent ultrasonic transducer device 500.

Ultrasonic transducer device 500 includes a membrane 508 overlying and attached to two inner anchors 510. It should be appreciated that membrane 508 spans all ultrasonic transducer devices 500 of the two-dimensional array of ultrasonic transducer devices 500. Inner anchors 510 may be made of electrically conducting materials, such as and without limitation, aluminum, molybdenum, or titanium. In some embodiments, inner anchors 510 may be made of dielectric materials, such as silicon dioxide, silicon nitride or aluminum oxide that have electrical connections along the sides or in vias through inner anchors 510, for electrically coupling electrodes 522, 524, and/or 526 to electrical wiring in substrate 540. For example, substrate 540 may include terminals for electrically coupling electrodes 522, 524, and/or 526 to control circuitry.

In various embodiments, substrate 540 may include at least one of, and without limitation, silicon or silicon nitride. It should be appreciated that substrate 540 may include electrical wirings and connection, such as aluminum or copper. In one embodiment, substrate 540 includes a CMOS logic wafer bonded to inner anchors 510. Membrane 508 includes a piezoelectric layer 514 and electrodes 522, 524, and 526, with electrodes 522 and 524 on the same side of piezoelectric layer 514 and electrodes 526 on the opposite side of piezoelectric layer 514 than electrodes 522 and 524. In some embodiments, membrane 308 further includes electrode 530 connected to ground. In accordance with some embodiments, membrane 508 further includes a structural layer 512 (e.g., a stiffening layer or a mechanical support layer) to mechanically stiffen membrane 508. In various embodiments, structural layer 512 may include at least one of, and without limitation, silicon, silicon oxide, silicon nitride, aluminum, molybdenum, titanium, etc. It should be appreciated that in accordance with various embodiments, membrane 508 can also include other layers (not shown), such as an acoustic coupling layer. The acoustic coupling layer is for supporting transmission of acoustic signals, and, if present, is above membrane 508. It should be appreciated that acoustic coupling layer can include air, liquid, gel-like materials, or other materials for supporting transmission of acoustic signals.

Figure 5B:
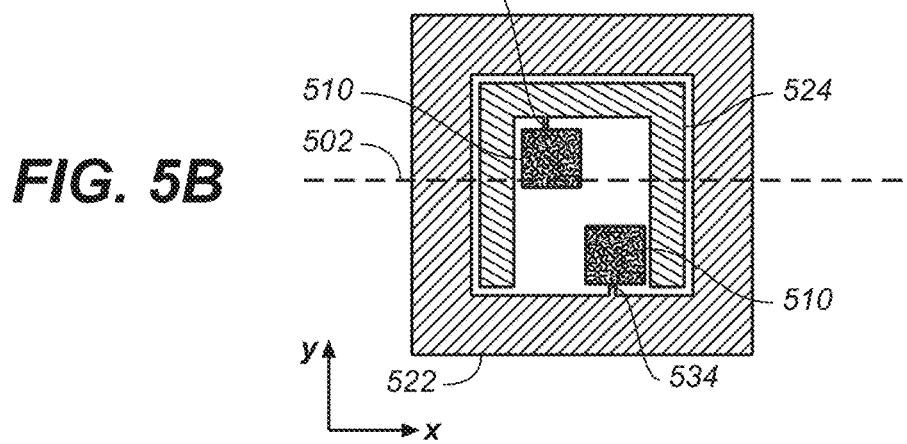
FIG. 5B is a diagram illustrating a top view of the electrode layout of an ultrasonic transducer device with two inner anchors and with two patterned electrodes placed at the bottom surface of the piezoelectric layer, according to some embodiments.

FIG. 5B is a diagram illustrating a top view of the electrode layout of an ultrasonic transducer device 500 with two inner anchors 510 and with two patterned electrodes 522 and 524 placed at the bottom surface of the piezoelectric layer 514, according to some embodiments. In the illustrated embodiment, one inner anchor 510 is connected to an electric connector 532 for connecting to electrode 522 to an electrical potential and another inner anchor 510 is connected to an electric connector 534 for connecting to electrode 524 to an electrical potential.

Figure 5C:
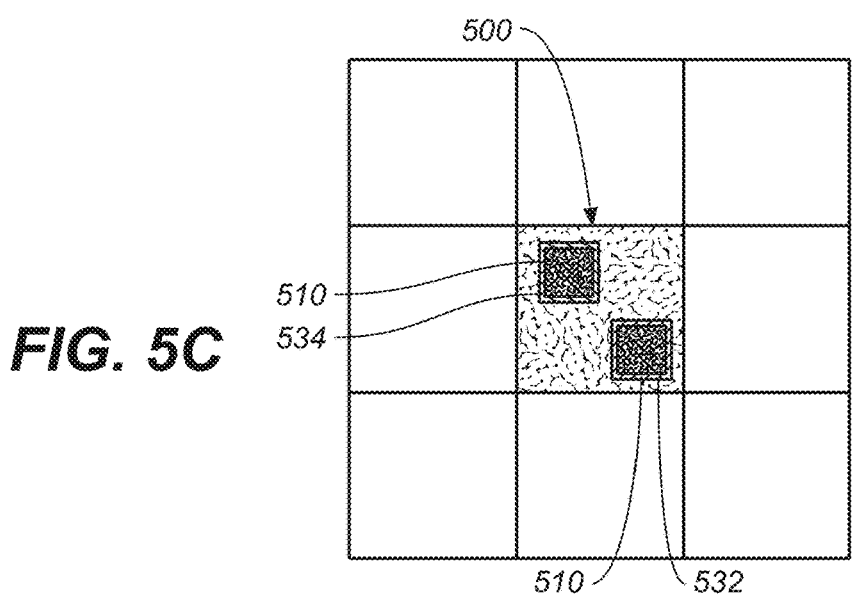
FIG. 5C is a diagram illustrating a top view of the anchor configuration of a two-dimensional array of ultrasonic transducer devices with two inner anchors, according to some embodiments.

In some embodiments, a plurality of ultrasonic transducer devices 500 are comprised within a two-dimensional (or one-dimensional) array of ultrasonic transducer devices 500. FIG. 5C is a diagram illustrating a top view of the anchor configuration of a two-dimensional array of ultrasonic transducer devices 500 with two inner anchors 510 per ultrasonic transducer device 500, according to some embodiments. It should be appreciated that FIG. 5C shows the anchor configuration for one ultrasonic transducer device 500 surrounded by other ultrasonic transducer devices 500 for which the anchor configuration is not shown.

In some embodiments, the array of ultrasonic transducer devices 500 may be coupled to a platen layer above an acoustic coupling layer for containing the acoustic coupling layer and providing a contact surface for a finger or other sensed object with the array of ultrasonic transducer devices 500. It should be appreciated that, in various embodiments, the acoustic coupling layer provides a contact surface, such that a platen layer is optional. It should be appreciated that the contact surface can be flat or of a varying thickness (e.g., curved).

Further, ultrasonic transducer device 500 comprises electrodes 522, 524, and 526 that supply and/or collect the electrical charge to/from piezoelectric layer 514. Electrodes 522, 524, and 526 can be connected to substrate 540 or the underlying circuitry via one or more terminals on substrate 540. In some embodiments, ground electrode 530 can be connected to substrate 540 or the underlying circuitry via one or more terminals on substrate 540. In the illustrated embodiment, one inner anchor 510 is connected to an electric connector 532 for connecting to electrode 522 to an electrical potential and another inner anchor 510 is connected to an electric connector 534 for connecting to electrode 524 to an electrical potential. Depending on the mode of operation, two or more electrodes may share a single terminal. It should be appreciated that electrodes 522 and 524 are patterned electrodes (e.g., a patterned layer). As an example, electrodes 522, 524, 526, and 530 can be comprised of almost any metal layers, such as, but not limited to, aluminum (Al), titanium (Ti), Molybdenum (Mo), etc.

In accordance with various embodiments, electrodes 522, 524, and/or 526 can be patterned in particular shapes (e.g., ring, circle, square, octagon, hexagon, etc.) that are coupled with the membrane 508. In some embodiments, electrodes 522 and 524 are coupled to different terminals and operate as separate electrodes, where electrode 526 is coupled to ground (GND) or other potential. In some embodiments, electrodes 530 and 526 are coupled to ground (GND). In accordance with some embodiments, electrode 522 is dedicated for use in a transmit operation for generating an ultrasonic signal and electrode 524 is dedicated for use in a receive operation for receiving a reflected ultrasonic signal.

In some embodiments, a plurality of ultrasonic transducer devices is comprised within a one-dimensional array of ultrasonic transducer devices. FIGS. 6A through 8C illustrates different anchor configurations of example one-dimensional arrays of ultrasonic transducer devices. It should be appreciated that the ultrasonic transducer devices of FIGS. 6A through 8C operate in a similar manner and include the same componentry as the ultrasonic transducer devices of FIGS. 1A through 5C (e.g., ultrasonic transducer devices 100, 200, 300, 400, and 500) with the exception of their use only within a one-dimensional array of ultrasonic transducer devices. As such, the ultrasonic transducer devices of FIGS. 6A through 8C each have two shared sides (e.g., sides adjacent to another ultrasonic transducer device) and exclusive sides (e.g., sides not adjacent to another ultrasonic transducer device), with the exception of ultrasonic transducer devices at the ends of the one-dimensional array having one shared side and three exclusive sides.

The ultrasonic transducer devices of FIGS. 6A through 8C employ a piezoelectric layer comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production (transmitting) and sensing (receiving). The piezoelectric layer can generate electric charges under mechanical stress and conversely experience a mechanical strain in the presence of an electric field. For example, the piezoelectric layer can sense mechanical vibrations caused by an ultrasonic signal and produce an electrical charge at the frequency (e.g., ultrasonic frequency) of the vibrations. Additionally, the piezoelectric layer can generate an ultrasonic wave by vibrating in an oscillatory fashion that might be at the same frequency (e.g., ultrasonic frequency) as an input current generated by an alternating current (AC) voltage applied across the piezoelectric layer. It should be appreciated that piezoelectric layer can include almost any material (or combination of materials) that exhibits piezoelectric properties. The polarization is directly proportional to the applied stress and is direction dependent so that compressive and tensile stresses results in electric fields of opposite polarizations.

Figure 6C:
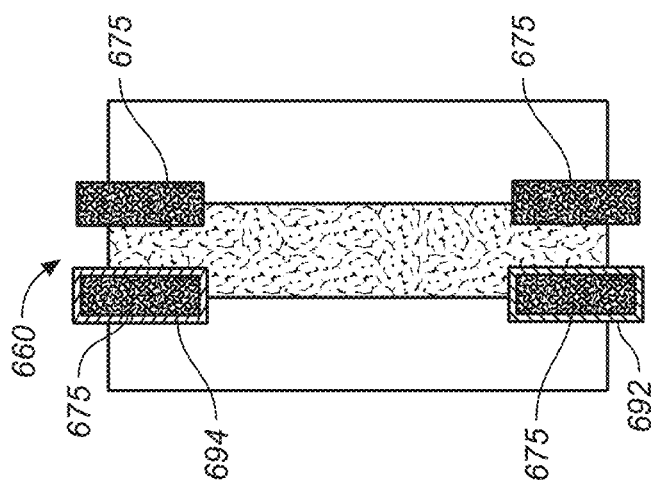
FIG. 6C is a diagram illustrating a top view of the anchor configuration of a one-dimensional array of ultrasonic transducer devices with four corner anchors, according to some embodiments.
Figure 6B:
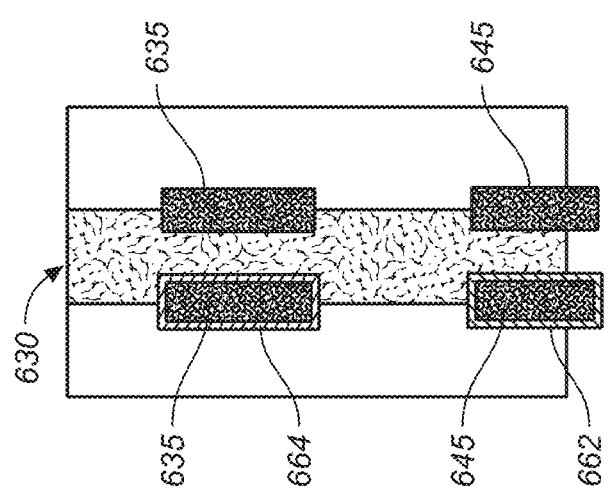
FIG. 6B is a diagram illustrating a top view of the anchor configuration of a one-dimensional array of ultrasonic transducer devices with two corner anchors and two shared side anchors, according to some embodiments.
Figure 6A:
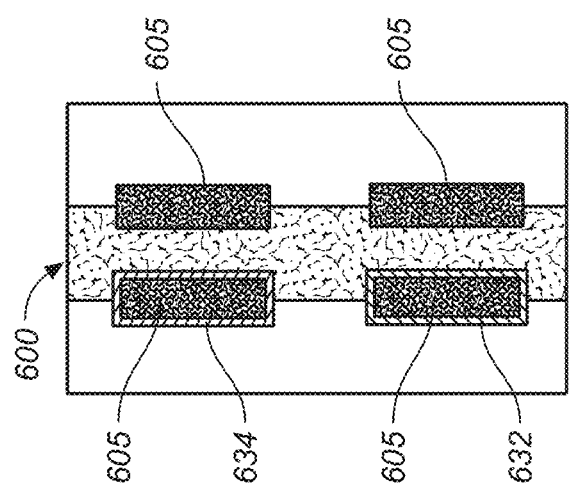
FIG. 6A is a diagram illustrating a top view of the anchor configuration of a one-dimensional array of ultrasonic transducer devices with four shared side anchors, according to some embodiments.

FIG. 6A is a diagram illustrating a top view of the anchor configuration of a one-dimensional array of ultrasonic transducer devices 600 with four shared side anchors 605, according to some embodiments. It should be appreciated that FIG. 6A shows the anchor configuration for one ultrasonic transducer device 600 surrounded by two other ultrasonic transducer devices 600 on each shared side for which the anchor configuration is not shown, apart from the shared side anchors 605. In some embodiments, ultrasonic transducer device 600 is a PMUT device.

Ultrasonic transducer device 600 is one ultrasonic transducer of a one-dimensional array of ultrasonic transducer devices 600, where each ultrasonic transducer includes a pair of electrodes to which electrical connections 632 and 634 are electrically coupled. The electrodes can be connected to a substrate or the underlying circuitry via one or more terminals on the substrate. In the illustrated embodiment, ultrasonic transducer device 600 has four shared side anchors 605, where a shared side anchor 605 is on a shared side of ultrasonic transducer device 600. Electrical connection 632 is for connecting one electrode to an electrical potential and electrical connection 634 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 600 includes a membrane overlying and attached to shared side anchors 605. It should be appreciated that the membrane spans all ultrasonic transducer devices 600 of the one-dimensional array of ultrasonic transducer devices 600. Shared side anchors 605 may be made of electrically conducting materials, such as and without limitation, aluminum, molybdenum, or titanium. In some embodiments, shared side anchors 605 may be made of dielectric materials, such as silicon dioxide, silicon nitride or aluminum oxide that have electrical connections 632 and 634 along the sides or in vias through shared side anchors 605, for electrically coupling electrodes to electrical wiring in the substrate. For example, the substrate may include terminals for electrically coupling the electrodes to control circuitry.

Ultrasonic transducer device 600 comprises electrodes that supply and/or collect the electrical charge to/from the piezoelectric layer. In the illustrated embodiment, one shared side anchor 605 is connected to an electrical connection 632 for connecting one electrode to an electrical potential and another shared side anchor 605 is connected to an electrical connection 634 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 632 is dedicated for use in a transmit operation for generating an ultrasonic signal and the electrode coupled to electrical connection 634 is dedicated for use in a receive operation for receiving a reflected ultrasonic signal.

FIG. 6B is a diagram illustrating a top view of the anchor configuration of a one-dimensional array of ultrasonic transducer devices 630 with two shared side anchors 635 and two corner anchors 645, according to some embodiments. It should be appreciated that FIG. 6B shows the anchor configuration for one ultrasonic transducer device 630 surrounded by two other ultrasonic transducer devices 630 on each shared side for which the anchor configuration is not shown, apart from the shared side anchors 635 and the corner anchors 645. In some embodiments, ultrasonic transducer device 630 is a PMUT device.

Ultrasonic transducer device 630 is one ultrasonic transducer of a one-dimensional array of ultrasonic transducer devices 630, where each ultrasonic transducer includes a pair of electrodes to which electrical connections 662 and 664 are electrically coupled. The electrodes can be connected to a substrate or the underlying circuitry via one or more terminals on the substrate. In the illustrated embodiment, ultrasonic transducer device 630 has two shared side anchors 635, where a side anchor 635 is on a shared side of ultrasonic transducer device 630, and two corner anchors 645, where a corner anchor is both on a shared side and on exclusive side of ultrasonic transducer device 630. Electrical connection 662 is for connecting one electrode to an electrical potential and electrical connection 664 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 630 includes a membrane overlying and attached to shared side anchors 635 and to corner anchors 645. It should be appreciated that the membrane spans all ultrasonic transducer devices 630 of the one-dimensional array of ultrasonic transducer devices 630. Shared side anchors 635 and corner anchors 645 may be made of electrically conducting materials, such as and without limitation, aluminum, molybdenum, or titanium. In some embodiments, shared side anchors 635 and corner anchors 645 may be made of dielectric materials, such as silicon dioxide, silicon nitride or aluminum oxide that have electrical connections 662 and 664 along the sides or in vias through shared side anchors 635 and corner anchors 645, for electrically coupling electrodes to electrical wiring in the substrate. For example, the substrate may include terminals for electrically coupling the electrodes to control circuitry.

Ultrasonic transducer device 630 comprises electrodes that supply and/or collect the electrical charge to/from the piezoelectric layer. In the illustrated embodiment, one shared side anchor 635 is connected to an electrical connection 664 for connecting one electrode to an electrical potential and one corner anchor 645 is connected to an electrical connection 662 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 662 is dedicated for use in a transmit operation for generating an ultrasonic signal and the electrode coupled to electrical connection 664 is dedicated for use in a receive operation for receiving a reflected ultrasonic signal.

FIG. 6C is a diagram illustrating a top view of the anchor configuration of a one-dimensional array of ultrasonic transducer devices 660 with four corner anchors 675, according to some embodiments. It should be appreciated that FIG. 6C shows the anchor configuration for one ultrasonic transducer device 660 surrounded by two other ultrasonic transducer devices 660 on each shared side for which the anchor configuration is not shown, apart from the corner anchors 675. In some embodiments, ultrasonic transducer device 660 is a PMUT device.

Ultrasonic transducer device 660 is one ultrasonic transducer of a one-dimensional array of ultrasonic transducer devices 660, where each ultrasonic transducer includes a pair of electrodes to which electrical connections 692 and 694 are electrically coupled. The electrodes can be connected to a substrate or the underlying circuitry via one or more terminals on the substrate. In the illustrated embodiment, ultrasonic transducer device 660 has four corner anchors 675, where a corner anchor 675 is on both a shared side and an exclusive side of ultrasonic transducer device 660. Electrical connection 692 is for connecting one electrode to an electrical potential and electrical connection 694 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 660 includes a membrane overlying and attached to corner anchors 675. It should be appreciated that the membrane spans all ultrasonic transducer devices 660 of the one-dimensional array of ultrasonic transducer devices 660. Corner anchors 675 may be made of electrically conducting materials, such as and without limitation, aluminum, molybdenum, or titanium. In some embodiments, corner anchors 675 may be made of dielectric materials, such as silicon dioxide, silicon nitride or aluminum oxide that have electrical connections 692 and 694 along the sides or in vias through corner anchors 675, for electrically coupling electrodes to electrical wiring in the substrate. For example, the substrate may include terminals for electrically coupling the electrodes to control circuitry.

Ultrasonic transducer device 660 comprises electrodes that supply and/or collect the electrical charge to/from the piezoelectric layer. In the illustrated embodiment, one corner anchor 675 is connected to an electrical connection 692 for connecting one electrode to an electrical potential and another corner anchor 675 is connected to an electrical connection 694 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 692 is dedicated for use in a transmit operation for generating an ultrasonic signal and the electrode coupled to electrical connection 694 is dedicated for use in a receive operation for receiving a reflected ultrasonic signal.

Figure 7B:
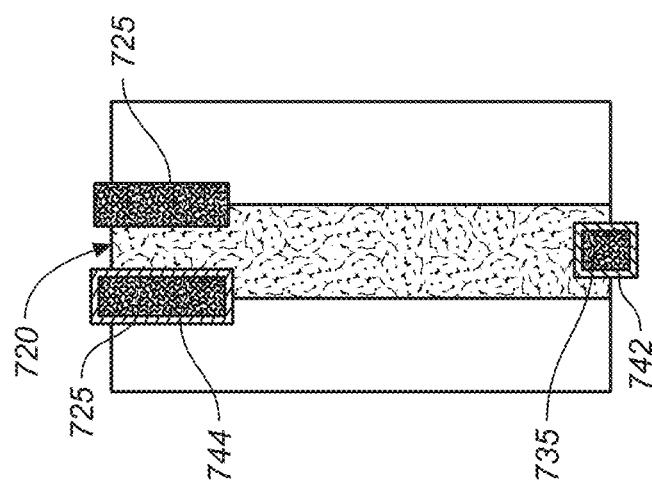
FIG. 7B is a diagram illustrating a top view of the anchor configuration of a one-dimensional array of ultrasonic transducer devices with two corner anchors and one exclusive side anchor, according to some embodiments.
Figure 7A:
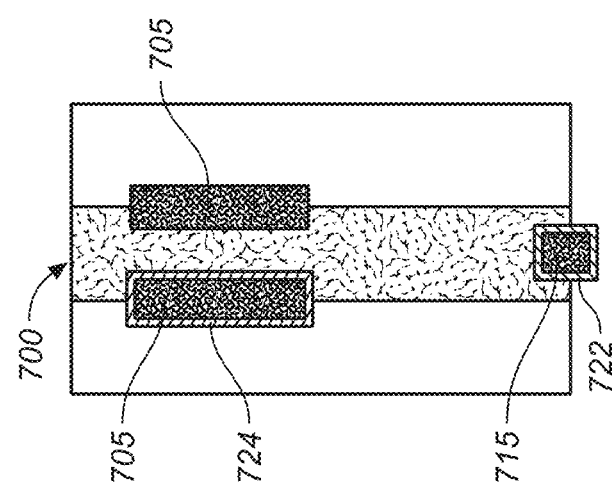
FIG. 7A is a diagram illustrating a top view of the anchor configuration of a one-dimensional array of ultrasonic transducer devices with two shared side anchors and one exclusive side anchor, according to some embodiments.

FIG. 7A is a diagram illustrating a top view of the anchor configuration of a one-dimensional array of ultrasonic transducer devices 700 with two shared side anchors 705 and one exclusive side anchor 715, according to some embodiments. It should be appreciated that FIG. 7A shows the anchor configuration for one ultrasonic transducer device 700 surrounded by two other ultrasonic transducer devices 700 on each shared side for which the anchor configuration is not shown, apart from the shared side anchors 705. In some embodiments, ultrasonic transducer device 700 is a PMUT device.

Ultrasonic transducer device 700 is one ultrasonic transducer of a one-dimensional array of ultrasonic transducer devices 700, where each ultrasonic transducer includes a pair of electrodes to which electrical connections 722 and 724 are electrically coupled. The electrodes can be connected to a substrate or the underlying circuitry via one or more terminals on the substrate. In the illustrated embodiment, ultrasonic transducer device 700 has two shared side anchors 705 and one excusive side anchor 715, where a shared side anchor 705 is on a shared side of ultrasonic transducer device 700 and an exclusive side anchor 715 is on an exclusive side of ultrasonic transducer device 700. Electrical connection 722 is for connecting one electrode to an electrical potential and electrical connection 724 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 700 includes a membrane overlying and attached to shared side anchors 705 and exclusive side anchor 715. It should be appreciated that the membrane spans all ultrasonic transducer devices 700 of the one-dimensional array of ultrasonic transducer devices 700. Shared side anchors 705 and exclusive side anchor 715 may be made of electrically conducting materials, such as and without limitation, aluminum, molybdenum, or titanium. In some embodiments, shared side anchors 705 and exclusive side anchor 715 may be made of dielectric materials, such as silicon dioxide, silicon nitride or aluminum oxide that have electrical connections 722 and 724 along the sides or in vias through shared side anchors 705 and/or exclusive side anchor 715, for electrically coupling electrodes to electrical wiring in the substrate. For example, the substrate may include terminals for electrically coupling the electrodes to control circuitry.

Ultrasonic transducer device 700 comprises electrodes that supply and/or collect the electrical charge to/from the piezoelectric layer. In the illustrated embodiment, exclusive side anchor 715 is connected to an electrical connection 722 for connecting one electrode to an electrical potential and one shared side anchor 705 is connected to an electrical connection 724 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 722 is dedicated for use in a transmit operation for generating an ultrasonic signal and the electrode coupled to electrical connection 724 is dedicated for use in a receive operation for receiving a reflected ultrasonic signal.

FIG. 7B is a diagram illustrating a top view of the anchor configuration of a one-dimensional array of ultrasonic transducer devices 720 with two corner anchors 725 and one exclusive side anchor 735, according to some embodiments. It should be appreciated that FIG. 7B shows the anchor configuration for one ultrasonic transducer device 720 surrounded by two other ultrasonic transducer devices 720 on each shared side for which the anchor configuration is not shown, apart from the corner anchors 725. In some embodiments, ultrasonic transducer device 720 is a PMUT device.

Ultrasonic transducer device 720 is one ultrasonic transducer of a one-dimensional array of ultrasonic transducer devices 720, where each ultrasonic transducer includes a pair of electrodes to which electrical connections 742 and 744 are electrically coupled. The electrodes can be connected to a substrate or the underlying circuitry via one or more terminals on the substrate. In the illustrated embodiment, ultrasonic transducer device 720 has two corner anchors 725 and one exclusive side anchor 735, where a corner anchor 725 is on both a shared side and an exclusive side of ultrasonic transducer device 720 and an exclusive side anchor 735 is on an exclusive side of ultrasonic transducer device 720. Electrical connection 742 is for connecting one electrode to an electrical potential and electrical connection 744 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 720 includes a membrane overlying and attached to corner anchors 725 and exclusive side anchor 735. It should be appreciated that the membrane spans all ultrasonic transducer devices 720 of the one-dimensional array of ultrasonic transducer devices 720. Corner anchors 725 and exclusive side anchor 735 may be made of electrically conducting materials, such as and without limitation, aluminum, molybdenum, or titanium. In some embodiments, corner anchors 725 and exclusive side anchor 735 may be made of dielectric materials, such as silicon dioxide, silicon nitride or aluminum oxide that have electrical connections 742 and 744 along the sides or in vias through corner anchors 725 and/or exclusive side anchor 735, for electrically coupling electrodes to electrical wiring in the substrate. For example, the substrate may include terminals for electrically coupling the electrodes to control circuitry.

Ultrasonic transducer device 720 comprises electrodes that supply and/or collect the electrical charge to/from the piezoelectric layer. In the illustrated embodiment, exclusive side anchor 735 is connected to an electrical connection 742 for connecting one electrode to an electrical potential and one corner anchor 725 is connected to an electrical connection 744 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 742 is dedicated for use in a transmit operation for generating an ultrasonic signal and the electrode coupled to electrical connection 744 is dedicated for use in a receive operation for receiving a reflected ultrasonic signal.

Figure 7D:
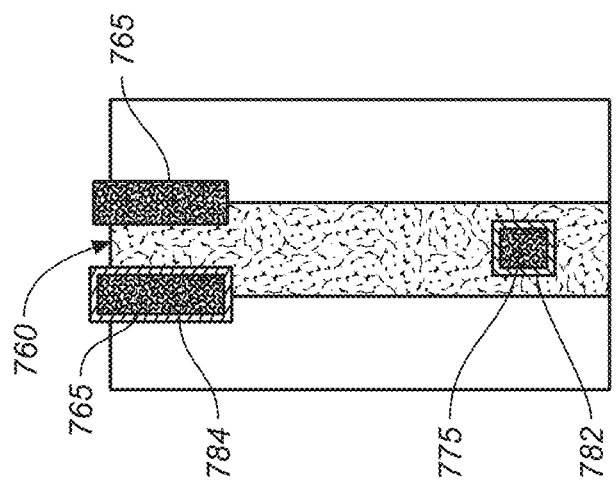
FIG. 7D is a diagram illustrating a top view of the anchor configuration of a one-dimensional array of ultrasonic transducer devices with two corner anchors and an inner anchor, according to some embodiments.
Figure 7C:
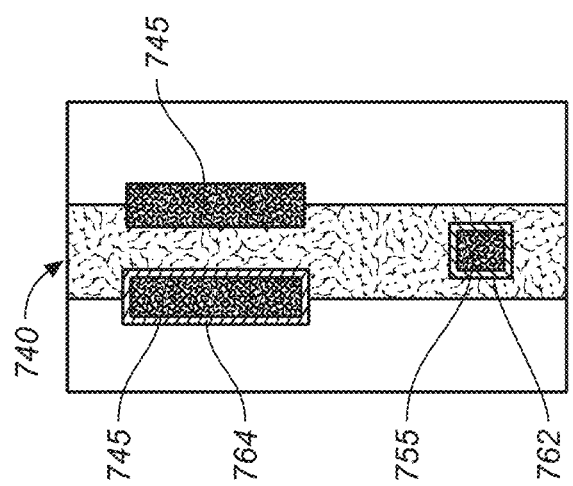
FIG. 7C is a diagram illustrating a top view of the anchor configuration of a one-dimensional array of ultrasonic transducer devices with two shared side anchors and an inner anchor, according to some embodiments.

FIG. 7C is a diagram illustrating a top view of the anchor configuration of a one-dimensional array of ultrasonic transducer devices 740 with two shared side anchors 745 and one inner anchor 755, according to some embodiments. It should be appreciated that FIG. 7C shows the anchor configuration for one ultrasonic transducer device 740 surrounded by two other ultrasonic transducer devices 740 on each shared side for which the anchor configuration is not shown, apart from the shared side anchors 745. In some embodiments, ultrasonic transducer device 740 is a PMUT device.

Ultrasonic transducer device 740 is one ultrasonic transducer of a one-dimensional array of ultrasonic transducer devices 740, where each ultrasonic transducer includes a pair of electrodes to which electrical connections 762 and 764 are electrically coupled. The electrodes can be connected to a substrate or the underlying circuitry via one or more terminals on the substrate. In the illustrated embodiment, ultrasonic transducer device 740 has two shared side anchors 745 and one inner anchor 755, where a shared side anchor 745 is on a shared side of ultrasonic transducer device 740 and an inner anchor 755 is positioned inside ultrasonic transducer device 740. Electrical connection 762 is for connecting one electrode to an electrical potential and electrical connection 764 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 740 includes a membrane overlying and attached to shared side anchors 745 and inner anchors 755. It should be appreciated that the membrane spans all ultrasonic transducer devices 740 of the one-dimensional array of ultrasonic transducer devices 740. Shared side anchors 745 and inner anchors 755 may be made of electrically conducting materials, such as and without limitation, aluminum, molybdenum, or titanium. In some embodiments, shared side anchors 745 and inner anchors 755 may be made of dielectric materials, such as silicon dioxide, silicon nitride or aluminum oxide that have electrical connections 762 and 764 along the sides or in vias through shared side anchors 745 and/or inner anchors 755, for electrically coupling electrodes to electrical wiring in the substrate. For example, the substrate may include terminals for electrically coupling the electrodes to control circuitry.

Ultrasonic transducer device 740 comprises electrodes that supply and/or collect the electrical charge to/from the piezoelectric layer. In the illustrated embodiment, inner anchor 755 is connected to an electrical connection 762 for connecting one electrode to an electrical potential and one shared side anchor 745 is connected to an electrical connection 764 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 762 is dedicated for use in a transmit operation for generating an ultrasonic signal and the electrode coupled to electrical connection 764 is dedicated for use in a receive operation for receiving a reflected ultrasonic signal.

FIG. 7D is a diagram illustrating a top view of the anchor configuration of a one-dimensional array of ultrasonic transducer devices 760 with two corner anchors 765 and one inner anchor 775, according to some embodiments. It should be appreciated that FIG. 7D shows the anchor configuration for one ultrasonic transducer device 760 surrounded by two other ultrasonic transducer devices 760 on each shared side for which the anchor configuration is not shown, apart from the corner anchors 765. In some embodiments, ultrasonic transducer device 760 is a PMUT device.

Ultrasonic transducer device 760 is one ultrasonic transducer of a one-dimensional array of ultrasonic transducer devices 760, where each ultrasonic transducer includes a pair of electrodes to which electrical connections 782 and 784 are electrically coupled. The electrodes can be connected to a substrate or the underlying circuitry via one or more terminals on the substrate. In the illustrated embodiment, ultrasonic transducer device 760 has two corner anchors 765 and inner anchor 775, where a corner anchor 765 is on both a shared side and an exclusive side of ultrasonic transducer device 760 and an inner anchor 775 is positioned inside the ultrasonic transducer device 760. Electrical connection 782 is for connecting one electrode to an electrical potential and electrical connection 784 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 760 includes a membrane overlying and attached to corner anchors 765 and inner anchors 775. It should be appreciated that the membrane spans all ultrasonic transducer devices 760 of the one-dimensional array of ultrasonic transducer devices 760. Corner anchors 765 and inner anchors 775 may be made of electrically conducting materials, such as and without limitation, aluminum, molybdenum, or titanium. In some embodiments, corner anchors 765 and inner anchors 775 may be made of dielectric materials, such as silicon dioxide, silicon nitride or aluminum oxide that have electrical connections 782 and 784 along the sides or in vias through corner anchors 765 and/or inner anchors 775, for electrically coupling electrodes to electrical wiring in the substrate. For example, the substrate may include terminals for electrically coupling the electrodes to control circuitry.

Ultrasonic transducer device 760 comprises electrodes that supply and/or collect the electrical charge to/from the piezoelectric layer. In the illustrated embodiment, inner anchor 775 is connected to an electrical connection 782 for connecting one electrode to an electrical potential and one corner anchor 765 is connected to an electrical connection 784 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 782 is dedicated for use in a transmit operation for generating an ultrasonic signal and the electrode coupled to electrical connection 784 is dedicated for use in a receive operation for receiving a reflected ultrasonic signal.

Figure 8C:
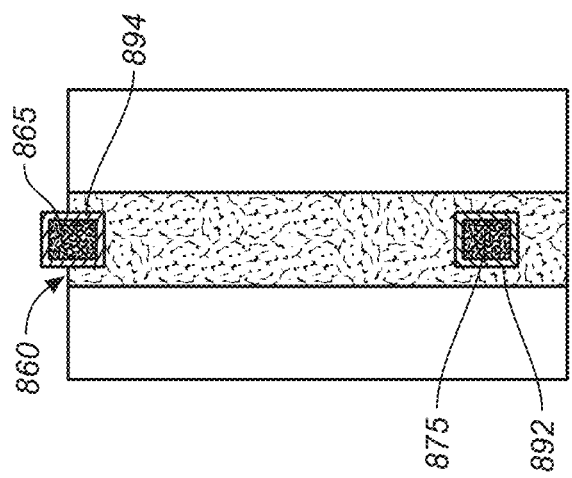
FIG. 8C is a diagram illustrating a top view of the anchor configuration of a one-dimensional array of ultrasonic transducer devices with one exclusive side anchor and one inner anchor, according to some embodiments.
Figure 8B:
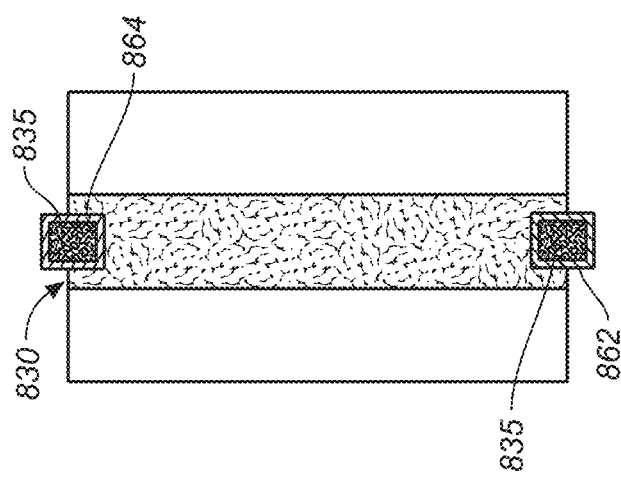
FIG. 8B is a diagram illustrating a top view of the anchor configuration of a one-dimensional array of ultrasonic transducer devices with two exclusive side anchors, according to some embodiments.
Figure 8A:
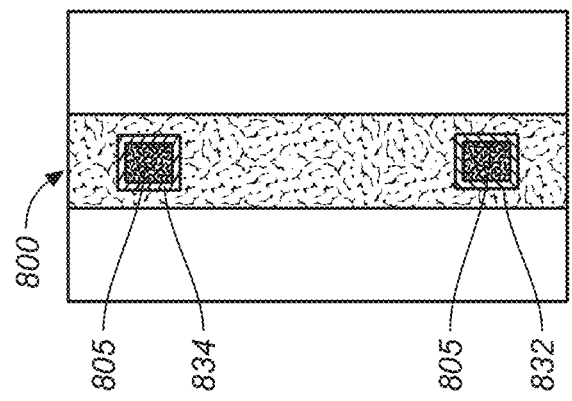
FIG. 8A is a diagram illustrating a top view of the anchor configuration of a one-dimensional array of ultrasonic transducer devices with two inner anchors, according to some embodiments.

FIG. 8A is a diagram illustrating a top view of the anchor configuration of a one-dimensional array of ultrasonic transducer devices 800 with two inner anchors 805, according to some embodiments. It should be appreciated that FIG. 8A shows the anchor configuration for one ultrasonic transducer device 800 surrounded by two other ultrasonic transducer devices 800 on each shared side for which the anchor configuration is not shown. In some embodiments, ultrasonic transducer device 800 is a PMUT device.

Ultrasonic transducer device 800 is one ultrasonic transducer of a one-dimensional array of ultrasonic transducer devices 800, where each ultrasonic transducer includes a pair of electrodes to which electrical connections 832 and 834 are electrically coupled. The electrodes can be connected to a substrate or the underlying circuitry via one or more terminals on the substrate. In the illustrated embodiment, ultrasonic transducer device 800 has two inner anchors 805, where an inner anchor 805 is positioned inside the ultrasonic transducer device 800. Electrical connection 832 is for connecting one electrode to an electrical potential and electrical connection 834 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 800 includes a membrane overlying and attached to two inner anchors 805. It should be appreciated that the membrane spans all ultrasonic transducer devices 800 of the one-dimensional array of ultrasonic transducer devices 800. Inner anchors 805 may be made of electrically conducting materials, such as and without limitation, aluminum, molybdenum, or titanium. In some embodiments, inner anchors 805 may be made of dielectric materials, such as silicon dioxide, silicon nitride or aluminum oxide that have electrical connections 832 and 834 along the sides or in vias through inner anchors 805, for electrically coupling electrodes to electrical wiring in the substrate. For example, the substrate may include terminals for electrically coupling the electrodes to control circuitry.

Ultrasonic transducer device 800 comprises electrodes that supply and/or collect the electrical charge to/from the piezoelectric layer. In the illustrated embodiment, one inner anchor 805 is connected to an electrical connection 832 for connecting one electrode to an electrical potential and another inner anchor 805 is connected to an electrical connection 834 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 832 is dedicated for use in a transmit operation for generating an ultrasonic signal and the electrode coupled to electrical connection 834 is dedicated for use in a receive operation for receiving a reflected ultrasonic signal.

FIG. 8B is a diagram illustrating a top view of the anchor configuration of a one-dimensional array of ultrasonic transducer devices 830 with two exclusive side anchors 835, according to some embodiments. It should be appreciated that FIG. 8B shows the anchor configuration for one ultrasonic transducer device 830 surrounded by two other ultrasonic transducer devices 830 on each shared side for which the anchor configuration is not shown. In some embodiments, ultrasonic transducer device 830 is a PMUT device.

Ultrasonic transducer device 830 is one ultrasonic transducer of a one-dimensional array of ultrasonic transducer devices 830, where each ultrasonic transducer includes a pair of electrodes to which electrical connections 862 and 864 are electrically coupled. The electrodes can be connected to a substrate or the underlying circuitry via one or more terminals on the substrate. In the illustrated embodiment, ultrasonic transducer device 830 has two exclusive side anchors 835, where exclusive side anchor 835 is on an exclusive side of ultrasonic transducer device 830. Electrical connection 862 is for connecting one electrode to an electrical potential and electrical connection 864 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 830 includes a membrane overlying and attached to exclusive side anchors 835. It should be appreciated that the membrane spans all ultrasonic transducer devices 830 of the one-dimensional array of ultrasonic transducer devices 830. Exclusive side anchors 835 may be made of electrically conducting materials, such as and without limitation, aluminum, molybdenum, or titanium. In some embodiments, exclusive side anchors 835 may be made of dielectric materials, such as silicon dioxide, silicon nitride or aluminum oxide that have electrical connections 862 and 864 along the sides or in vias through exclusive side anchors 835, for electrically coupling electrodes to electrical wiring in the substrate. For example, the substrate may include terminals for electrically coupling the electrodes to control circuitry.

Ultrasonic transducer device 830 comprises electrodes that supply and/or collect the electrical charge to/from the piezoelectric layer. In the illustrated embodiment, one exclusive side anchor 835 is connected to an electrical connection 862 for connecting one electrode to an electrical potential and another exclusive side anchor 835 is connected to an electrical connection 864 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 862 is dedicated for use in a transmit operation for generating an ultrasonic signal and the electrode coupled to electrical connection 864 is dedicated for use in a receive operation for receiving a reflected ultrasonic signal.

FIG. 8C is a diagram illustrating a top view of the anchor configuration of a one-dimensional array of ultrasonic transducer devices 860 with one exclusive side anchor 865 and one inner anchor 875, according to some embodiments. It should be appreciated that FIG. 8C shows the anchor configuration for one ultrasonic transducer device 860 surrounded by two other ultrasonic transducer devices 860 on each shared side for which the anchor configuration is not shown. In some embodiments, ultrasonic transducer device 860 is a PMUT device.

Ultrasonic transducer device 860 is one ultrasonic transducer of a one-dimensional array of ultrasonic transducer devices 860, where each ultrasonic transducer includes a pair of electrodes to which electrical connections 892 and 894 are electrically coupled. The electrodes can be connected to a substrate or the underlying circuitry via one or more terminals on the substrate. In the illustrated embodiment, ultrasonic transducer device 860 has one exclusive side anchor 865, where exclusive side anchor 865 is on an exclusive side of ultrasonic transducer device 860, and one inner anchor 875, where inner anchor 875 is positioned inside the ultrasonic transducer device 860. Electrical connection 892 is for connecting one electrode to an electrical potential and electrical connection 894 is for connecting another electrode to an electrical potential. It should be appreciated that the electrodes are patterned electrodes (e.g., a patterned layer). As an example, the electrodes can be comprised of almost any metal layers, such as, but not limited to, aluminum (Al), titanium (Ti), Molybdenum (Mo), etc.

Ultrasonic transducer device 860 includes a membrane overlying and attached to exclusive side anchor 865 and to inner anchor 875. It should be appreciated that the membrane spans all ultrasonic transducer devices 860 of the one-dimensional array of ultrasonic transducer devices 860. Exclusive side anchor 865 and inner anchor 875 may be made of electrically conducting materials, such as and without limitation, aluminum, molybdenum, or titanium. In some embodiments, exclusive side anchor 865 and inner anchor 875 may be made of dielectric materials, such as silicon dioxide, silicon nitride or aluminum oxide that have electrical connections 892 and 894 along the sides or in vias through exclusive side anchors 865 or inner anchor 875, for electrically coupling electrodes to electrical wiring in the substrate. For example, the substrate may include terminals for electrically coupling the electrodes to control circuitry.

Ultrasonic transducer device 860 comprises electrodes that supply and/or collect the electrical charge to/from the piezoelectric layer. In the illustrated embodiment, exclusive side anchor 865 is connected to an electrical connection 894 for connecting one electrode to an electrical potential and inner anchor 875 is connected to an electrical connection 892 for connecting another electrode to an electrical potential. Depending on the mode of operation, two or more electrodes may share a single terminal. In accordance with various embodiments, the electrodes can be patterned in particular shapes (e.g., ring, circle, square, octagon, hexagon, etc.) that are coupled with the membrane. In some embodiments, the electrodes are coupled to different terminals and operate as separate electrodes. In accordance with some embodiments, the electrode coupled to electrical connection 892 is dedicated for use in a transmit operation for generating an ultrasonic signal and the electrode coupled to electrical connection 894 is dedicated for use in a receive operation for receiving a reflected ultrasonic signal.

Figure 9A:
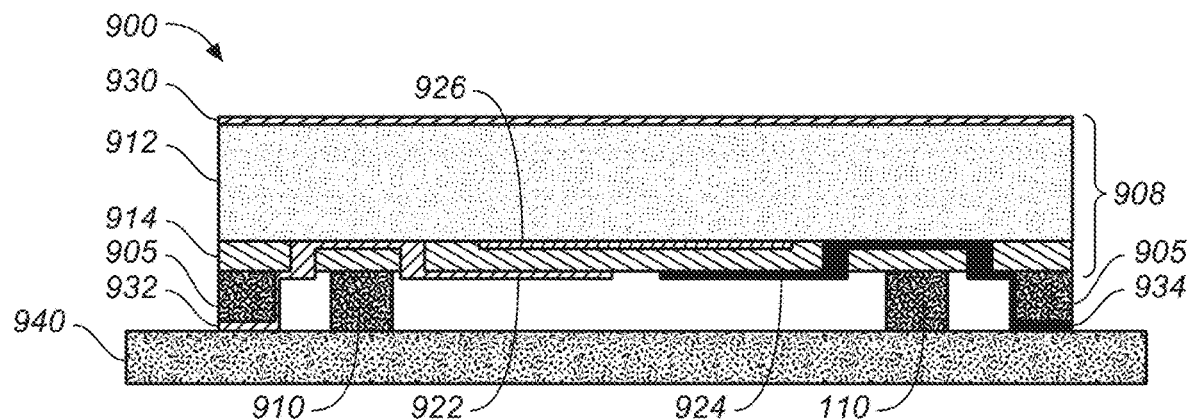
FIG. 9A is a diagram illustrating a side view cross-section of an ultrasonic transducer device with external anchors connecting multiple non-overlapping sensing electrodes, according to some embodiments.

Ultrasonic Transducer Devices Including External Anchors Providing Electrical Connections to Multiple Electrodes FIG. 9A is a diagram illustrating a side view cross-section of an ultrasonic transducer device 900 with support anchors 910 and external anchors 905 connecting multiple non-overlapping electrodes 922 and 924, according to some embodiments. In some embodiments, ultrasonic transducer device 900 is a PMUT device. In some embodiments, ultrasonic transducer device 900 is one ultrasonic transducer of a one-dimensional or two-dimensional array of ultrasonic transducer devices 900, where each ultrasonic transducer includes a pair of electrodes 922 and 924 and a sensing area between support anchors 910.

Ultrasonic transducer device 900 includes a membrane 908 overlying and attached to external anchors 905 and support anchors 910. It should be appreciated that membrane 908 spans all ultrasonic transducer devices 900 of a one-dimensional or two-dimensional array of ultrasonic transducer devices 900. External anchors 905 and support anchors 910 may be made of electrically conducting materials, such as and without limitation, aluminum, molybdenum, or titanium. In some embodiments, external anchors 905 and support anchors 910 may be made of dielectric materials, such as silicon dioxide, silicon nitride or aluminum oxide that have electrical connections along the sides or in vias through external anchors 905 and/or support anchors 910, for electrically coupling electrodes 922, 924, and/or 926 to electrical wiring in substrate 940. For example, substrate 940 may include terminals for electrically coupling electrodes 922, 924, and/or 926 to control circuitry.

In various embodiments, substrate 940 may include at least one of, and without limitation, silicon or silicon nitride. It should be appreciated that substrate 940 may include electrical wirings and connection, such as aluminum or copper. In one embodiment, substrate 940 includes a CMOS logic wafer bonded to external anchors 905 and support anchors 910. Membrane 908 includes a piezoelectric layer 914 and electrodes 922, 924, and 926. In accordance with some embodiments, membrane 908 further includes a structural layer 912 (e.g., a stiffening layer or a mechanical support layer) to mechanically stiffen membrane 908. In various embodiments, structural layer 912 may include at least one of, and without limitation, silicon, silicon oxide, silicon nitride, aluminum, molybdenum, titanium, etc. In some embodiments, membrane 908 also includes a ground electrode 930 placed at the opposite side of the cavity. It should be appreciated that in accordance with various embodiments, membrane 908 can also include other layers (not shown), such as an acoustic coupling layer. Electrode 922 is routed along or through one external anchor 905, through vias 932 of piezoelectric layer 914 on either side of one support anchor 910, and positioned at the bottom of piezoelectric layer 914 in the sensing region of the transducer defined by support anchors 910. Electrode 924 is routed along or through the other external anchor 905, through vias 934 of piezoelectric layer 914 on either side of the other support anchor 910, and positioned at the bottom of piezoelectric layer 914 in the sensing region of the transducer defined by support anchor 910 on the same side of piezoelectric layer 914, such that electrode 924 is next to and non-overlapping with electrode 922.

Electrodes 922, 924, 926, and 930 supply and/or collect the electrical charge to/from piezoelectric layer 914. Electrodes 922, 924, 926, and 930 can be connected to substrate 940 or the underlying circuitry via one or more terminals on substrate 940. In the illustrated embodiment, one external anchor 905 is used for routing to electrode 922 to an electrical potential and another external anchor is used for routing to electrode 924 to an electrical potential. Depending on the mode of operation, two or more electrodes may share a single terminal. It should be appreciated that electrodes 922, 924, and 926, are patterned electrodes (e.g., a patterned layer), while electrode 930 is a continuous electrode across all ultrasonic transducer devices 900 of a one-dimensional or two-dimensional array of ultrasonic transducer devices 900. As an example, electrodes 922, 924, 926, and 930 can be comprised of almost any metal layers, such as, but not limited to, aluminum (Al), titanium (Ti), Molybdenum (Mo), etc.

In accordance with various embodiments, electrodes 922, 924, and/or 926, can be patterned in particular shapes (e.g., ring, circle, square, octagon, hexagon, etc.) that are coupled with the membrane 908. In some embodiments, electrodes 922 and 924 are coupled to different terminals and operate as separate electrodes, where electrodes 926 and 930 are coupled to ground (GND) or other potential. In accordance with some embodiments, electrode 922 is dedicated for use in a transmit operation for generating an ultrasonic signal and electrode 924 is dedicated for use in a receive operation for receiving a reflected ultrasonic signal.

Figure 9B:
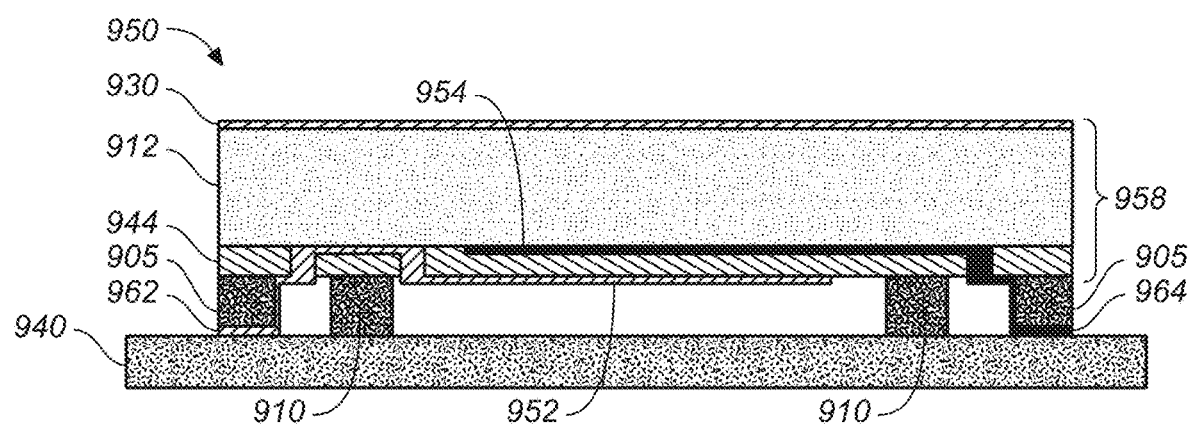
FIG. 9B is a diagram illustrating a side view cross-section of an ultrasonic transducer device with external anchors connecting multiple overlapping sensing electrodes, according to some embodiments.

FIG. 9B is a diagram illustrating a side view cross-section of an ultrasonic transducer device 950 with external anchors 905 and multiple overlapping sensing electrodes 952 and 954, according to some embodiments. In some embodiments, ultrasonic transducer device 950 is a PMUT device. In some embodiments, ultrasonic transducer device 950 is one ultrasonic transducer of a one-dimensional or two-dimensional array of ultrasonic transducer devices 950, where each ultrasonic transducer is defined by each pair of electrodes 952 and 954 and a sensing area between support anchors 910.

Ultrasonic transducer device 950 includes a membrane 958 overlying and attached to external anchors 905 and support anchors 910. It should be appreciated that membrane 958 spans all ultrasonic transducer devices 950 a one-dimensional or two-dimensional array of ultrasonic transducer devices 950. External anchors 905 and support anchors 910 may be made of electrically conducting materials, such as and without limitation, aluminum, molybdenum, or titanium. In some embodiments, external anchors 905 and support anchors 910 may be made of dielectric materials, such as silicon dioxide, silicon nitride or aluminum oxide that have electrical connections along the sides or in vias through external anchors 905 and support anchors 910, for electrically coupling electrodes 952 and/or 954 to electrical wiring in substrate 940. For example, substrate 940 may include terminals for electrically coupling electrodes 952 and/or 954 to control circuitry.

Membrane 958 includes piezoelectric layer 944 and electrodes 952 and 954. In accordance with some embodiments, membrane 908 further includes structural layer 912 (e.g., a stiffening layer or a mechanical support layer) to mechanically stiffen membrane 908. In various embodiments, structural layer 912 may include at least one of, and without limitation, silicon, silicon oxide, silicon nitride, aluminum, molybdenum, titanium, etc. It should be appreciated that in accordance with various embodiments, membrane 908 can also include other layers (not shown), such as an acoustic coupling layer. Electrode 952 is routed along or through one external anchor 905, through vias 962 of piezoelectric layer 944 on either side of one support anchor 910, and positioned under piezoelectric layer 944 in the sensing region defined by support anchor 910. Electrode 954 is routed along or through the other external anchor 905, through via 964 of piezoelectric layer 944 on the outer side of the other support anchor 910, and positioned over piezoelectric layer 944 in the sensing region defined by support anchor 910 on the opposite side of piezoelectric layer 944 as electrode 952, such that electrode 954 is overlapping with electrode 952.

Electrodes 952 and 954 supply and/or collect the electrical charge to/from piezoelectric layer 944. Electrodes 952 and 954 can be connected to substrate 940 or the underlying circuitry via one or more terminals on substrate 940. In the illustrated embodiment, one external anchor 905 is used for routing to electrode 952 to an electrical potential and another external anchor is used for routing to electrode 954 to an electrical potential. Depending on the mode of operation, two or more electrodes may share a single terminal. It should be appreciated that electrodes 952, and 954 are patterned electrodes (e.g., a patterned layer). As an example, electrodes 952 and 954 can be comprised of almost any metal layers, such as, but not limited to, aluminum (Al), titanium (Ti), Molybdenum (Mo), etc.

In accordance with various embodiments, electrodes 952 and/or 954 can be patterned in particular shapes (e.g., ring, circle, square, octagon, hexagon, etc.) that are coupled with the membrane 958. In some embodiments, electrodes 952 and 954 are coupled to different terminals and operate as separate electrodes. In accordance with some embodiments, electrode 952 is dedicated for use in a transmit operation for generating an ultrasonic signal and electrode 954 is dedicated for use in a receive operation for receiving a reflected ultrasonic signal.

Figure 10A:
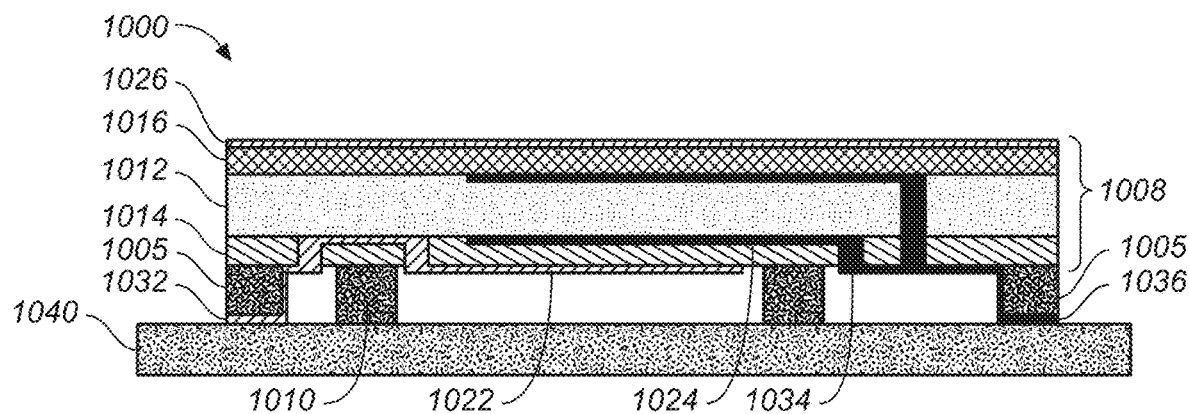
FIG. 10A is a diagram illustrating a side view cross-section of dual layer ultrasonic transducer device with two external anchors connecting two electrodes, according to some embodiments.

FIG. 10A is a diagram illustrating a side view cross-section of a dual piezoelectric layer ultrasonic transducer device 1000 with two external anchors 1005 connecting two electrodes 1022 and 1024, according to some embodiments. In some embodiments, ultrasonic transducer device 1000 is a PMUT device. In some embodiments, ultrasonic transducer device 1000 is one ultrasonic transducer of a one-dimensional or two-dimensional array of ultrasonic transducer devices 1000, where each ultrasonic transducer includes a pair of electrodes 1022 and 1024 and a sensing area between support anchors 1010.

Ultrasonic transducer device 1000 includes a membrane 1008 overlying and attached to external anchors 1005 and support anchors 1010. It should be appreciated that membrane 1008 spans all ultrasonic transducer devices 1000 a one-dimensional or two-dimensional array of ultrasonic transducer devices 1000. External anchors 1005 and support anchors 1010 may be made of electrically conducting materials, such as and without limitation, aluminum, molybdenum, or titanium. In some embodiments, external anchors 1005 and support anchors 1010 may be made of dielectric materials, such as silicon dioxide, silicon nitride or aluminum oxide that have electrical connections along the sides or in vias through external anchors 1005 and/or support anchors 1010, for electrically coupling electrodes 1022, 1024, and/or 1026 to electrical wiring in substrate 1040. For example, substrate 1040 may include terminals for electrically coupling electrodes 1022, 1024, and/or 1026 to control circuitry.

In various embodiments, substrate 1040 may include at least one of, and without limitation, silicon or silicon nitride. It should be appreciated that substrate 1040 may include electrical wirings and connection, such as aluminum or copper. In one embodiment, substrate 1040 includes a CMOS logic wafer bonded to external anchors 1005 and support anchors 1010. Membrane 1008 includes a piezoelectric layer 1014, a piezoelectric layer 1016, a buffer layer 1012, and electrodes 1022 and 1024. In some embodiments, membrane 1008 also includes a ground electrode 1026 placed at the opposite side of the cavity. Buffer layer 1012 is positioned between piezoelectric layers 1014 and 1016. Electrode 1022 is routed along or through one external anchor 1005, through vias 1032 of piezoelectric layer 1014 on either side of one support anchor 1010, and positioned at the bottom of piezoelectric layer 1014 in the sensing region defined by support anchors 1010. Electrode 1024 is routed along or through the other external anchor 1005, through via 1034 of piezoelectric layer 1014 on one side of the other support anchor 1010 and through via 1036 of piezoelectric layer 1014 and buffer layer 1012 on one side of the other support anchor 1010, and positioned on both sides of buffer layer 1012 in the sensing region defined by support anchor 1010, such that electrode 1024 has two portions overlapping with electrode 1022.

Buffer layer 1012 separates piezoelectric layers 1014 and 1016. Buffer layer 1012 can be comprised of materials such as, but not limited to, silicon, silicon oxide, polysilicon, silicon nitride, or any non-conducting oxide layer (or stacks of layers). Moreover, it should be appreciated that the buffer material can be application specific, e.g., selected based on a desired frequency of operation of dual layer ultrasonic transducer device 1000. For example, buffer layer 1012 can be a metal. It should be appreciated that the stiffer the material of buffer layer 1012, the higher the frequency.

Buffer layer 1012 allows for improved tuning of the transmit and receive operations, by enhancing the performance of the transmit and receive operations. The frequency can be tuned according to thickness of buffer layer 1012 to improve the figure of merit (FOM) of dual layer ultrasonic transducer device 1000. Moreover, the neutral axis can be designed to not be in the middle of membrane 1008 so as to achieve a better FOM. Buffer layer 1012 also supports tuning of the thicknesses and materials of piezoelectric layers 1014 and 1016.

Electrodes 1022, 1024, and 1026 supply and/or collect the electrical charge to/from piezoelectric layers 1014 and 1016. Electrodes 1022, 1024, and 1026 can be connected to substrate 1040 or the underlying circuitry via one or more terminals on substrate 1040. In the illustrated embodiment, one external anchor 1005 is used for routing to electrode 1022 to an electrical potential and another external anchor 1005 is used for routing to electrode 1024 to an electrical potential. Depending on the mode of operation, two or more electrodes may share a single terminal. It should be appreciated that electrodes 1022 and 1024 are patterned electrodes (e.g., a patterned layer), while electrode 1026 is continuous electrode across all ultrasonic transducer devices 1000 of a one-dimensional or two-dimensional array of ultrasonic transducer devices 1000. As an example, electrodes 1022, 1024, and 1026 can be comprised of almost any metal layers, such as, but not limited to, aluminum (Al), titanium (Ti), Molybdenum (Mo), etc.

In accordance with various embodiments, electrodes 1022 and/or 1024 can be patterned in particular shapes (e.g., ring, circle, square, octagon, hexagon, etc.) that are coupled with the membrane 1008. In some embodiments, electrodes 1022 and 1024 are coupled to different terminals and operate as separate electrodes, where electrode 1026 is coupled to ground (GND) or other potential. In accordance with some embodiments, electrode 1022 is dedicated for use in a transmit operation for generating an ultrasonic signal and electrode 1024 is dedicated for use in a receive operation for receiving a reflected ultrasonic signal.

Figure 10B:
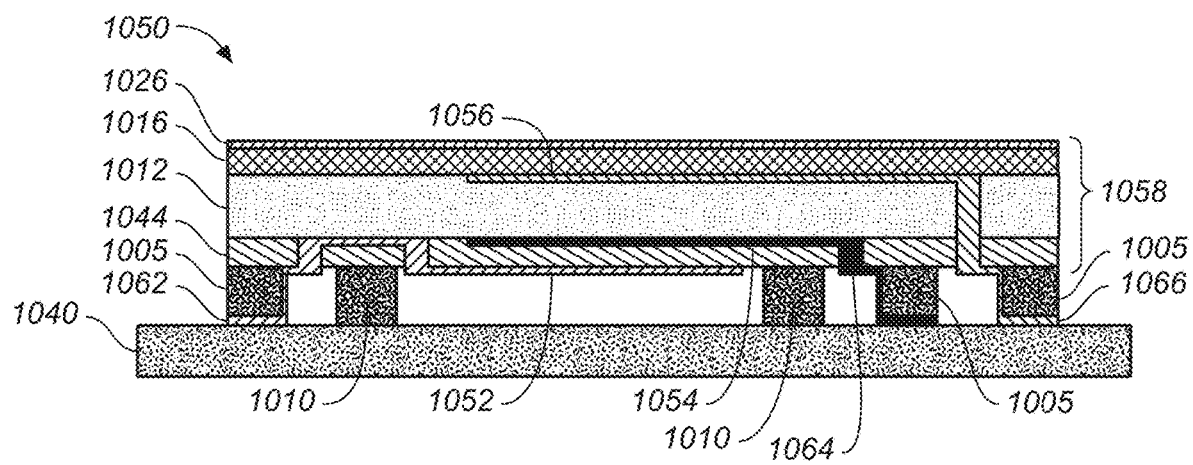
FIG. 10B is a diagram illustrating a side view cross-section of dual layer ultrasonic transducer device with three external anchors connecting three electrodes, according to some embodiments.

FIG. 10B is a diagram illustrating a side view cross-section of a dual layer ultrasonic transducer device 1050 with three external anchors 1005 and three electrodes 1052, 1054, and 1056, according to some embodiments. In some embodiments, ultrasonic transducer device 1050 is a PMUT device. In some embodiments, ultrasonic transducer device 1050 is one ultrasonic transducer of a one-dimensional or two-dimensional array of ultrasonic transducer devices 1050, where each ultrasonic transducer is defined by electrodes 1052, 1054, and 1056 and a sensing area between support anchors 1010.

Ultrasonic transducer device 1050 includes a membrane 1058 overlying and attached to external anchors 1005 and support anchors 1010. It should be appreciated that membrane 1058 spans all ultrasonic transducer devices 1050 a one-dimensional or two-dimensional array of ultrasonic transducer devices 1050. External anchors 1005 and support anchors 1010 may be made of electrically conducting materials, such as and without limitation, aluminum, molybdenum, or titanium. In some embodiments, external anchors 1005 and support anchors 1010 may be made of dielectric materials, such as silicon dioxide, silicon nitride or aluminum oxide that have electrical connections along the sides or in vias through external anchors 1005 and support anchors 1010, for electrically coupling electrodes 1052, 1054, 1056, and/or 1026 to electrical wiring in substrate 1040. For example, substrate 1040 may include terminals for electrically coupling electrodes 1052, 1054, 1056, and/or 1026 to control circuitry.

In various embodiments, substrate 1040 may include at least one of, and without limitation, silicon or silicon nitride. It should be appreciated that substrate 1040 may include electrical wirings and connection, such as aluminum or copper. In one embodiment, substrate 1040 includes a CMOS logic wafer bonded to external anchors 1005 and support anchors 1010. Membrane 1058 includes piezoelectric layer 1044, piezoelectric layer 1016, buffer layer 1012, and electrodes 1052, 1054, 1056, and 1026. Buffer layer 1012 is positioned between piezoelectric layers 1044 and 1016. Electrode 1052 is routed along or through one external anchor 1005, through vias 1062 of piezoelectric layer 1044 on either side of one support anchor 1010, and positioned under piezoelectric layer 1044 in the sensing region defined by support anchor 1010. Electrode 1054 is routed along or through another external anchor 1005, through via 1064 of piezoelectric layer 1044, and positioned over piezoelectric layer 1044 in the sensing region defined by support anchors 1010 on the opposite side of piezoelectric layer 1044 as electrode 1052, such that electrode 1054 is overlapping with electrode 1052. Electrode 1056 is routed along or through another external anchor 1005, through via 1066 of piezoelectric layer 1044 and buffer layer 1012, and positioned over buffer layer 1012 in the sensing region defined by support anchors 1010 on the opposite side of buffer layer 1012 as electrode 1054, such that electrode 1056 is overlapping with electrode 1054 and 1052.

Buffer layer 1012 separates piezoelectric layers 1044 and 1016. Buffer layer 1012 can be comprised of materials such as, but not limited to, silicon, silicon oxide, polysilicon, silicon nitride, or any non-conducting oxide layer (or stacks of layers). Moreover, it should be appreciated that the buffer material can be application specific, e.g., selected based on a desired frequency of operation of dual layer ultrasonic transducer device 1050. For example, buffer layer 1012 can be a metal. It should be appreciated that the stiffer the material of buffer layer 1012, the higher the frequency.

Buffer layer 1012 allows for improved tuning of the transmit and receive operations, by enhancing the performance of the transmit and receive operations. The frequency can be tuned according to thickness of buffer layer 1012 so as to optimize the thicknesses of piezoelectric layers 1044 and 1016 to improve the figure of merit (FOM) of dual layer ultrasonic transducer device 1050. Moreover, the neutral axis can be designed to not be in the middle of membrane 1058 so as to achieve a better FOM. Buffer layer 1012 also supports tuning of the thicknesses and materials of piezoelectric layers 1044 and 1016.

Electrodes 1052, 1054, 1056, and 1026 supply and/or collect the electrical charge to/from piezoelectric layers 1044 and 1016. Electrodes 1052, 1054, 1056, and 1026 can be connected to substrate 1040 or the underlying circuitry via one or more terminals on substrate 1040. In the illustrated embodiment, one external anchor 1005 is used for routing to electrode 1052 to an electrical potential, a second external anchor 1005 is used for routing to electrode 1054 to an electrical potential, and a third external anchor 1005 is used for routing to electrode 1056 to an electrical potential. Depending on the mode of operation, two or more electrodes may share a single terminal. It should be appreciated that electrodes 1052, 1054, 1056, and 1026 are patterned electrodes (e.g., a patterned layer). As an example, electrodes 1052, 1054, 1056, and 1026 can be comprised of almost any metal layers, such as, but not limited to, aluminum (Al), titanium (Ti), Molybdenum (Mo), etc.

In accordance with various embodiments, electrodes 1052, 1054, 1056, and/or 1026 can be patterned in particular shapes (e.g., ring, circle, square, octagon, hexagon, etc.) that are coupled with the membrane 1058. In some embodiments, electrodes 1052, 1054, and 1056 are coupled to different terminals and operate as separate electrodes, where electrode 1026 is coupled to ground (GND) or other potential. In accordance with some embodiments, electrode 1052 is dedicated for use in a transmit operation for generating an ultrasonic signal and electrode 1054 is dedicated for use in a receive operation for receiving a reflected ultrasonic signal.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated examples of the claimed subject matter.

The aforementioned systems and components have been described with respect to interaction between several components. It can be appreciated that such systems and components can include those components or specified subcomponents, some of the specified components or subcomponents, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. An ultrasonic transducer array comprising:
   a substrate;
   a membrane overlying the substrate, the membrane configured to allow movement at ultrasonic frequencies, the membrane comprising:
      a piezoelectric layer;
      a plurality of first electrodes; and
      a plurality of second electrodes;
      wherein each ultrasonic transducer of a plurality of ultrasonic transducers comprises at least a first electrode of the plurality of first electrodes and at least a second electrode of the plurality of second electrodes; and
   a plurality of anchors connected to the substrate and connected to the membrane, the plurality of anchors defining a cavity between the substrate and the membrane, the plurality of anchors comprising:
      a first anchor comprising a first electrical connection for electrically coupling at least one first electrode to control circuitry; and
      a second anchor comprising a second electrical connection for electrically coupling at least one second electrode to the control circuitry.

2. The ultrasonic transducer array of claim 1, wherein the first electrical connection is for controlling the at least one first electrode during a transmit operation and the second electrical connection is for controlling the at least one second electrode during a receive operation.

3. The ultrasonic transducer array of claim 1, wherein the ultrasonic transducer array is a two-dimensional array of ultrasonic transducers.

4. The ultrasonic transducer array of claim 3, wherein the plurality of anchors comprises:
   corner anchors located at corners of the plurality of ultrasonic transducers such that a corner anchor is shared by adjacent ultrasonic transducers of the plurality of ultrasonic transducers.

5. The ultrasonic transducer array of claim 3, wherein the plurality of anchors comprises:
   side anchors located at sides of the plurality of ultrasonic transducers such that a side anchor is shared by two ultrasonic transducers of the plurality of ultrasonic transducers.

6. The ultrasonic transducer array of claim 3, wherein the plurality of anchors comprises:
   inner anchors located within an ultrasonic transducer of the plurality of ultrasonic transducers such that an inner anchor is dedicated to one ultrasonic transducer of the plurality of ultrasonic transducers.

7. The ultrasonic transducer array of claim 3, wherein the plurality of anchors comprises:
   one corner anchor for each corner of the plurality of ultrasonic transducers such that a corner anchor is shared by adjacent ultrasonic transducers of the plurality of ultrasonic transducers, wherein the first anchor is a corner anchor such that the first electrical connection is electrically coupled to the first electrode of one ultrasonic transducer; and
   at least one inner anchor located within an ultrasonic transducer of the plurality of ultrasonic transducers such that an inner anchor is dedicated to one ultrasonic transducer of the plurality of ultrasonic transducers, wherein the second anchor is an inner anchor such that the second electrical connection is electrically coupled to one second electrode of the one ultrasonic transducer.

8. The ultrasonic transducer array of claim 3, wherein the plurality of anchors comprises:
   at least two side anchors located at sides of the plurality of ultrasonic transducers such that a side anchor is shared by two ultrasonic transducers of the plurality of ultrasonic transducers, wherein the first anchor is a side anchor such that the first electrical connection is electrically coupled to the first electrode of one ultrasonic transducer; and
   at least one inner anchor located within an ultrasonic transducer of the plurality of ultrasonic transducers such that an inner anchor is dedicated to one ultrasonic transducer of the plurality of ultrasonic transducers, wherein the second anchor is an inner anchor such that the second electrical connection is electrically coupled to one second electrode of the one ultrasonic transducer.

9. The ultrasonic transducer array of claim 3, wherein the plurality of anchors comprises:
   one corner anchor for each corner of the plurality of ultrasonic transducers such that a corner anchor is shared by adjacent ultrasonic transducers of the plurality of ultrasonic transducers, wherein the first anchor is a corner anchor such that the first electrical connection is electrically coupled to one first electrode of one ultrasonic transducer; and at least two side anchors located at sides of the plurality of ultrasonic transducers such that a side anchor is shared by two ultrasonic transducers of the plurality of ultrasonic transducers, wherein the second anchor is a side anchor such that the second electrical connection is electrically coupled to one second electrode of the one ultrasonic transducer.

10. The ultrasonic transducer array of claim 3, wherein the plurality of anchors comprises:

at least four side anchors located at sides of the plurality of ultrasonic transducers such that a side anchor is shared by two ultrasonic transducers of the plurality of ultrasonic transducers, wherein the first anchor and the second anchor are side anchors such that the first electrical connection is electrically coupled to one first electrode of one ultrasonic transducer and the second electrical connection is electrically coupled to one second electrode of the one ultrasonic transducer, wherein the first anchor and second anchor are on adjacent sides of the ultrasonic transducer.

11. The ultrasonic transducer array of claim 3, wherein the plurality of anchors comprises:

at least two inner anchors located within an ultrasonic transducer of the plurality of ultrasonic transducers such that an inner anchor is dedicated to one ultrasonic transducer of the plurality of ultrasonic transducers, wherein the first anchor and the second anchor are inner anchors such that the first electrical connection is electrically coupled to one first electrode of one ultrasonic transducer and the second electrical connection is electrically coupled to one second electrode of the one ultrasonic transducer.

12. The ultrasonic transducer array of claim 1, wherein the ultrasonic transducer array is a one-dimensional array of ultrasonic transducers.

13. The ultrasonic transducer array of claim 12, wherein the plurality of anchors comprises:

at least four shared side anchors located on shared sides of an ultrasonic transducer of the plurality of ultrasonic transducers such that a shared side is shared by two adjacent ultrasonic transducers, wherein the first anchor and the second anchor are shared side anchors such that the first electrical connection is electrically coupled to at least one first electrode of one ultrasonic transducer and the second electrical connection is electrically coupled to at least one second electrode of the one ultrasonic transducer.

14. The ultrasonic transducer array of claim 12, wherein the plurality of anchors comprises:

at least two shared side anchors located on shared sides of an ultrasonic transducer of the plurality of ultrasonic transducers such that a shared side is shared by two adjacent ultrasonic transducers, wherein the first anchor is a shared side anchor such that the first electrical connection is electrically coupled to at least one first electrode of one ultrasonic transducer; and at least two corner anchors located at the corners of an ultrasonic transducer of the plurality of ultrasonic transducers such that a corner is shared by two adjacent ultrasonic transducers, wherein the second anchor is a corner anchor such that the second electrical connection is electrically coupled to at least one second electrode of the one ultrasonic transducer.

15. The ultrasonic transducer array of claim 12, wherein the plurality of anchors comprises:

four corner anchors located at the corners of an ultrasonic transducer of the plurality of ultrasonic transducers such that a corner is shared by two adjacent ultrasonic transducers, wherein the first anchor and the second anchor are corner anchors such that the first electrical connection is electrically coupled to at least one first electrode of one ultrasonic transducer and the second electrical connection is electrically coupled to at least one second electrode of the one ultrasonic transducer.

16. The ultrasonic transducer array of claim 12, wherein the plurality of anchors comprises:

at least two shared side anchors located on shared sides of an ultrasonic transducer of the plurality of ultrasonic transducers such that a shared side is shared by two adjacent ultrasonic transducers, wherein the first anchor is a shared side anchor such that the first electrical connection is electrically coupled to at least one first electrode of one ultrasonic transducer; and at least one exclusive side anchor located on exclusive sides of an ultrasonic transducer of the plurality of ultrasonic transducers such that an exclusive side is a side that is not shared by any ultrasonic transducers of the plurality of ultrasonic transducers, wherein the second anchor is an exclusive side anchor such that the second electrical connection is electrically coupled to at least one second electrode of the one ultrasonic transducer.

17. The ultrasonic transducer array of claim 12, wherein the plurality of anchors comprises:

at least two corner anchors located at the corners of an ultrasonic transducer of the plurality of ultrasonic transducers such that a corner is shared by two adjacent ultrasonic transducers, wherein the first anchor is a corner anchor such that the first electrical connection is electrically coupled to at least one first electrode of one ultrasonic transducer; and at least one exclusive side anchor located on exclusive sides of an ultrasonic transducer of the plurality of ultrasonic transducers such that an exclusive side is a side that is not shared by any ultrasonic transducers of the plurality of ultrasonic transducers, wherein the second anchor is an exclusive side anchor such that the second electrical connection is electrically coupled to at least one second electrode of the one ultrasonic transducer.

18. The ultrasonic transducer array of claim 12, wherein the plurality of anchors comprises:

at least two shared side anchors located on shared sides of an ultrasonic transducer of the plurality of ultrasonic transducers such that a shared side is shared by two adjacent ultrasonic transducers, wherein the first anchor is a side anchor such that the first electrical connection is electrically coupled to at least one first electrode of one ultrasonic transducer; and at least one inner anchor located within an ultrasonic transducer of the plurality of ultrasonic transducers such that an inner anchor is dedicated to one ultrasonic transducer of the plurality of ultrasonic transducers, wherein the second anchor is an inner anchor such that the second electrical connection is electrically coupled to one second electrode of the one ultrasonic transducer.

19. The ultrasonic transducer array of claim 12, wherein the plurality of anchors comprises:

at least two corner anchors located at the corners of an ultrasonic transducer of the plurality of ultrasonic transducers such that a corner is shared by two adjacent ultrasonic transducers of the plurality of ultrasonic transducers, wherein the first anchor is a corner anchor such that the first electrical connection is electrically coupled to at least one first electrode of one ultrasonic transducer; and at least one inner anchor located within an ultrasonic transducer of the plurality of ultrasonic transducers such that an inner anchor is dedicated to one ultrasonic transducer of the plurality of ultrasonic transducers, wherein the second anchor is an inner anchor such that the second electrical connection is electrically coupled to one second electrode of the one ultrasonic transducer.

20. The ultrasonic transducer array of claim 12, wherein the plurality of anchors comprises:

at least two inner anchors located within an ultrasonic transducer of the plurality of ultrasonic transducers such that an inner anchor is dedicated to one ultrasonic transducer of the plurality of ultrasonic transducers, wherein the first and the second anchors are inner anchors such that the first electrical connection is electrically coupled to one first electrode of one ultrasonic transducer and the second electrical connection is electrically coupled to one second electrode of the one ultrasonic transducer.

21. The ultrasonic transducer array of claim 12, wherein the plurality of anchors comprises:

at least two exclusive side anchors located on exclusive sides of an ultrasonic transducer of the plurality of ultrasonic transducers not shared by other ultrasonic transducers of the plurality of ultrasonic transducers such that an exclusive side anchor is dedicated to one ultrasonic transducer of the plurality of ultrasonic transducers, wherein the first and the second anchors are exclusive side anchors such that the first electrical connection is electrically coupled to one first electrode of one ultrasonic transducer and the second electrical connection is electrically coupled to one second electrode of the one ultrasonic transducer.

22. The ultrasonic transducer array of claim 12, wherein the plurality of anchors comprises:

at least one exclusive side anchor located on exclusive sides of an ultrasonic transducer of the plurality of ultrasonic transducers not shared by other ultrasonic transducers of the plurality of ultrasonic transducers such that an exclusive side anchor is dedicated to one ultrasonic transducer of the plurality of ultrasonic transducers, wherein the first anchor is an exclusive side anchor such that the first electrical connection is electrically coupled to at least one first electrode of one ultrasonic transducer; and at least one inner anchor located within an ultrasonic transducer of the plurality of ultrasonic transducers such that an inner anchor is dedicated to one ultrasonic transducer of the plurality of ultrasonic transducers, wherein the second anchor is an inner anchor such that the second electrical connection is electrically coupled to one second electrode of the one ultrasonic transducer.

* * * * *